US010639149B2

(12) United States Patent
Braido et al.

(10) Patent No.: US 10,639,149 B2
(45) Date of Patent: May 5, 2020

(54) SUTURELESS PROSTHETIC HEART VALVE

(71) Applicant: St. Jude Medical, Cardiology Division, Inc., St. Paul, MN (US)

(72) Inventors: Peter N. Braido, Wyoming, MN (US); Chad Joshua Green, Forest Lake, MN (US); Neelakantan Saikrishnan, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 15/743,131

(22) PCT Filed: Jun. 30, 2016

(86) PCT No.: PCT/US2016/040392
§ 371 (c)(1),
(2) Date: Jan. 9, 2018

(87) PCT Pub. No.: WO2017/011199
PCT Pub. Date: Jan. 19, 2017

(65) Prior Publication Data
US 2019/0099265 A1    Apr. 4, 2019

Related U.S. Application Data

(60) Provisional application No. 62/193,184, filed on Jul. 16, 2015.

(51) Int. Cl.
*A61F 2/24* (2006.01)
*A61F 2/86* (2013.01)
*A61F 2/848* (2013.01)

(52) U.S. Cl.
CPC .......... *A61F 2/2418* (2013.01); *A61F 2/2409* (2013.01); *A61F 2/86* (2013.01);
(Continued)

(58) Field of Classification Search
CPC ........ A61F 2/2418; A61F 2/2409; A61F 2/86; A61F 2002/8483; A61F 2220/0016; A61F 2250/0069
See application file for complete search history.

(56) References Cited

U.S. PATENT DOCUMENTS 3,657,744 A    4/1972  Ersek
4,275,469 A    6/1981  Gabbay
(Continued)

FOREIGN PATENT DOCUMENTS

DE    10121210 A1    11/2002
DE    19857887 B4     5/2005
(Continued)

OTHER PUBLICATIONS

Ruiz, Carlos, Overview of PRE-CE Mark Transcatheter Aortic Valve Technologies, Euro PCR dated May 25, 2010.
(Continued)

*Primary Examiner* — Christopher D. Prone
*Assistant Examiner* — Tiffany P Shipmon
(74) *Attorney, Agent, or Firm* — Lerner, David, Littenberg, Krumholz & Mentlik, LLP

(57) ABSTRACT

A prosthetic heart valve for replacing a native valve includes a stent extending between an inflow end and an outflow end, and a valve assembly disposed within the stent. The prosthetic heart valve may include a supra-annular feature configured to anchor and seal the prosthetic valve above the native valve annulus and a sub-annular feature configured to anchor and seal the prosthetic valve below the native valve annulus. Each of the sub-annular feature and the supra-annular feature may be a sealing ring or a strut that extends radially outward from the stent. The prosthetic heart valve may be implanted in the patient via a sutureless approach
(Continued)

and provide anchoring in a variety of patient populations, including those with resected native valve leaflets.

9 Claims, 15 Drawing Sheets

(52) U.S. Cl.
CPC ............... *A61F 2002/8483* (2013.01); *A61F 2220/0016* (2013.01); *A61F 2250/0069* (2013.01)

(56) References Cited

U.S. PATENT DOCUMENTS

| | | | |
|---|---|---|---|
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,415,664 A | 5/1995 | Pinchuk | |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,458,153 B1 | 10/2002 | Bailey et al. | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,857,845 B2 | 12/2010 | Stacchino et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| D684,692 S | 6/2013 | Braido | |
| 8,840,661 B2 | 9/2014 | Manasse | |
| 8,840,663 B2 | 9/2014 | Salahieh et al. | |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2005/0096726 A1 | 5/2005 | Sequin et al. | |
| 2005/0137695 A1 | 6/2005 | Salahieh et al. | |
| 2005/0137697 A1 | 6/2005 | Salahieh et al. | |
| 2005/0240200 A1 | 10/2005 | Bergheim | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1 | 8/2006 | Stacchino et al. | |
| 2006/0195180 A1 | 8/2006 | Kheradvar et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2007/0010876 A1* | 1/2007 | Salahieh ............... | A61F 2/2418 623/2.11 |
| 2007/0027534 A1 | 2/2007 | Bergheim | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0112309 A1 | 4/2009 | Jaramillo et al. | |
| 2009/0138079 A1 | 5/2009 | Tuval et al. | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0185277 A1 | 7/2010 | Braido et al. | |
| 2010/0191326 A1 | 7/2010 | Alkhatib | |
| 2010/0204781 A1 | 8/2010 | Alkhatib | |

(56) References Cited

U.S. PATENT DOCUMENTS

| | | |
|---|---|---|
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2012/0215303 A1 | 8/2012 | Quadri et al. |
| 2012/0303116 A1 | 11/2012 | Gorman, III et al. |
| 2013/0190862 A1* | 7/2013 | Pintor .................. A61F 2/2403 623/2.18 |
| 2014/0330366 A1* | 11/2014 | Dehdashtian ......... A61F 2/2433 623/2.11 |
| 2014/0330368 A1* | 11/2014 | Gloss .................... A61F 2/2418 623/2.11 |
| 2015/0142104 A1 | 5/2015 | Braido |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1 926 455 A2 | 6/2008 |
| FR | 2847800 A1 | 6/2004 |
| FR | 2850008 A1 | 7/2004 |
| JP | 2012504031 | 2/2012 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 0149213 A2 | 7/2001 |
| WO | 01054625 A1 | 8/2001 |
| WO | 01056500 A2 | 8/2001 |
| WO | 01076510 A2 | 10/2001 |
| WO | 0236048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 07071436 A2 | 6/2007 |
| WO | 08070797 A2 | 6/2008 |
| WO | 2009026563 A2 | 2/2009 |
| WO | 2009045331 A1 | 4/2009 |
| WO | 10/008549 A1 | 1/2010 |
| WO | 10008548 A2 | 1/2010 |
| WO | 10096176 A1 | 8/2010 |
| WO | 10098857 A1 | 9/2010 |
| WO | 2011072084 A2 | 6/2011 |
| WO | 2011112706 A2 | 9/2011 |
| WO | 2013177684 A1 | 12/2013 |
| WO | 2015077274 A1 | 5/2015 |

OTHER PUBLICATIONS

Percutaneous aortic valve replacement: resection before implantation, 836-840, Quaden, Rene et al., European J. of Cardio-thoracic Surgery, 27 (2005).

Catheter-implanted prosthetic heart valves, Knudsen, L.L., et al., The International Journal of Artificial Organs, vol. 16, No. 5 1993, pp. 253-262.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

Is it Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

"Direct-Access Valve Replacement", Christoph H. Huber, et al., Journal of the American College of Cardiology, vol. 46, No. 2, (Jul. 19, 2005).

"Percutaneous Aortic Valve Implantation Retrograde From the Femoral Artery", John G. Webb et al., Circulation, 2006; 113:842-850 (Feb. 6, 2006).

"Minimally invasive cardiac surgery", M. J. Mack, Surgical Endoscopy, 2006, 20:S488-S492, DOI: 10.1007/s00464-006-0110-8 (presented Apr. 24, 2006).

"Transapical Transcatheter Aortic Valve Implantation in Humans", Samuel V. Lichtenstein et al., Circulation. 2006; 114: 591-596 (Jul. 31, 2006).

"Transapical approach for sutureless stent-fixed aortic valve implantation: experimental results"; Th. Walther et al., European Journal of Cardio-thoracic Surgery 29 (2006) 703-708 (Jan. 30, 2006).

"Transapical aortic valve implantation: an animal feasibility study"; Todd M. Dewey et al., The annals of thoracic surgery 2006; 82: 110-6 (Feb. 13, 2006).

Textbook "Transcatheter Valve Repair", 2006, pp. 165-186.

"Closed heart surgery: Back to the future", Samuel V. Lichtenstein, The Journal of Thoracic and Cardiovascular Surgery, vol. 131, No. 5, pp. 941-943.

International Search Report for PCT/US2016/040392 dated Sep. 21, 2016.

* cited by examiner

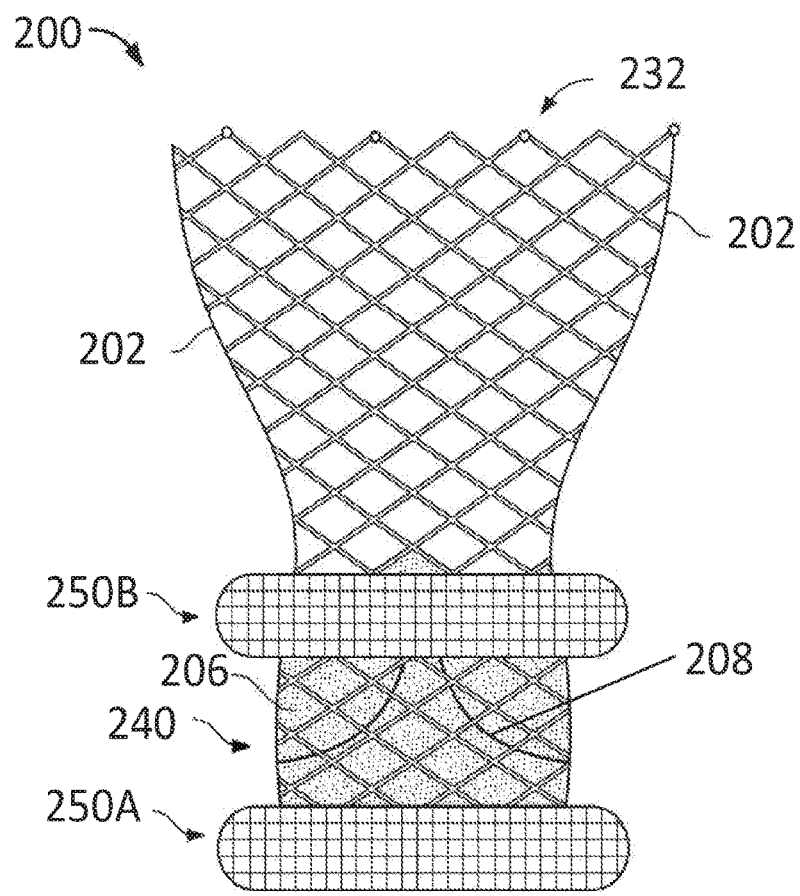
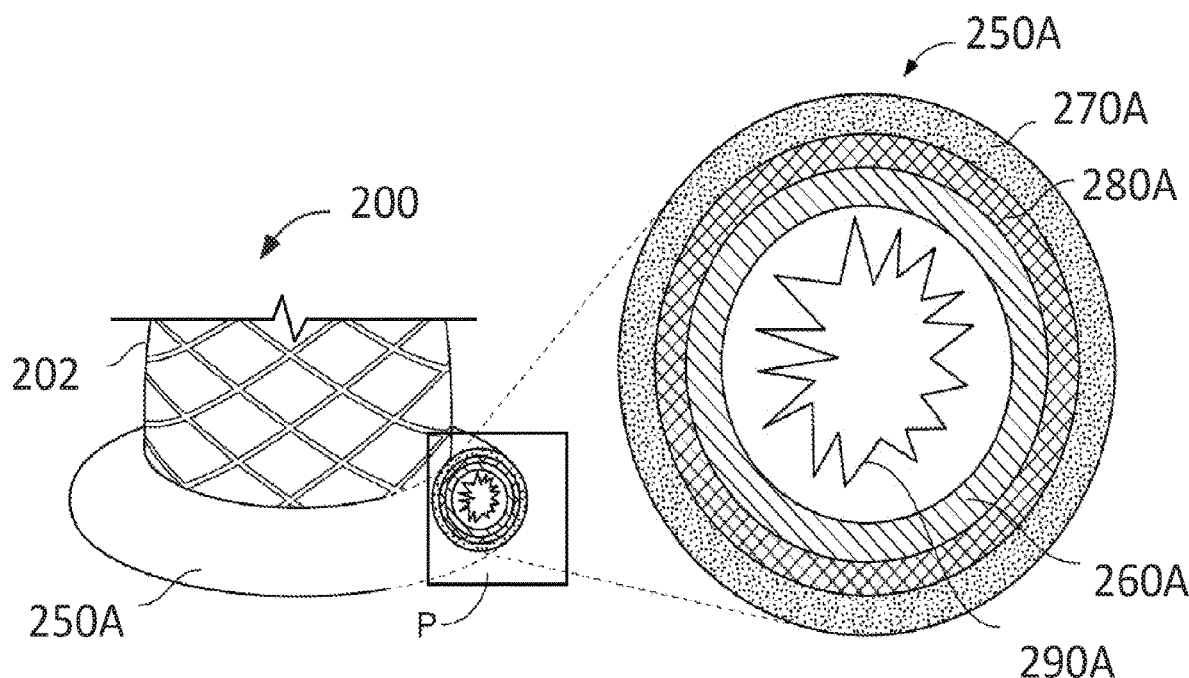
FIG. 2A
FIG. 2B

SUTURELESS PROSTHETIC HEART VALVE

CROSS-REFERENCE TO RELATED APPLICATIONS

This application is a national phase entry under 35 U.S.C. § 371 of International Application No. PCT/US2016/040392 filed Jun. 30, 2016, published in English, which claims the benefit of the filing date of U.S. Provisional Patent Application No. 62/193,184 filed Jul. 16, 2015, the disclosures of which are both hereby incorporated by reference herein.

BACKGROUND

The present disclosure relates to heart valve replacement and, in particular, to prosthetic heart valves. More particularly, the present disclosure relates to prosthetic heart valves with paravalvular leak prevention features.

Prosthetic heart valves may generally belong to one of three categories: surgical valves, transcatheter valves, and sutureless valves. Surgical valves generally are not collapsible, are implanted using full open-chest, open-heart surgery, and are held in place with sutures. Transcatheter valves, on the other hand, are typically collapsible to a relatively small circumferential size and can be delivered into a patient by a minimally invasive procedure through the use of a tube-like delivery apparatus such as a catheter, a trocar, a laparoscopic instrument, or the like. This collapsibility can avoid the need for the more invasive procedures employed for surgical vales. Although transcatheter valves do not employ sutures to secure the valve in position, "sutureless valves" generally refer to valves that are surgically implanted using an open chest procedure, but, as the name implies, are held in place without sutures.

Transcatheter prosthetic heart valves typically take the form of a valve structure mounted on a stent. There are two common types of stents on which the valve structures are ordinarily mounted: a self-expanding stent and a balloon-expandable stent. To place such valves into a delivery apparatus and ultimately into a patient, the valve is first collapsed or crimped to reduce its circumferential size.

When a collapsed prosthetic valve has reached the desired implantation site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as a sheath covering the valve is withdrawn.

In contrast to transcatheter valves, surgical valves and sutureless valves are typically delivered to a patient via open-heart surgery. Surgical valves are usually delivered to the site of implantation and a portion of the surgical valve, typically an outer rim, is sutured to patient tissue. Sutureless valves, on the other hand, typically include a stent, with features such as radial expandability or other additional attachment features, to anchor the valve in place without the need for sutures. Because sutureless valves do not require lengthy suturing to patient anatomy, they are generally implanted in less time than surgical valves, resulting in less time on a bypass machine and a reduced risk of infection.

BRIEF SUMMARY

According to one embodiment of the disclosure a prosthetic heart valve for replacing a native valve includes a stent extending between an inflow end and an outflow end, the stent including an annulus section adjacent the inflow end. A plurality of first struts are connected to the stent and are configured to extend radially outwardly from the stent when in a relaxed condition. A plurality of second struts are connected to the stent and are configured to extend radially outwardly form from the stent when in the relaxed condition. The plurality of first struts are spaced from the plurality of second struts in a longitudinal direction of the stent. A valve assembly is disposed within the stent.

According to another embodiment of the disclosure, a prosthetic heart valve includes a stent extending from an inflow end to an outflow end, and a first sealing ring coupled to the stent adjacent the inflow end of the stent. The first sealing ring includes a first tube extending circumferentially around the stent. A second sealing ring is coupled the stent, the second sealing ring including a second tube extending circumferentially around the stent. The second sealing ring is spaced from the first sealing ring in a longitudinal direction of the stent. A valve assembly is disposed within the stent.

According to still a further embodiment of the disclosure, a prosthetic heart valve includes a first valve anchoring feature spaced apart from a second valve anchoring feature. A method of implanting the prosthetic heart valve in a patient includes inserting the prosthetic heart valve into the patient's cardiovascular system while coupled to a valve holder. The prosthetic heart valve is advanced to a position adjacent a native valve annulus in the patient so that the first valve anchoring feature is disposed on a first side of the native valve annulus and the second valve anchoring feature is disposed on a second side of the native valve annulus opposite the first side. The prosthetic heart valve is released from the valve holder, and the valve holder is removed from the patient.

BRIEF DESCRIPTION OF THE DRAWINGS

FIG. 2A is a highly schematic side view of one embodiment of a heart valve having a pair of sealing rings.

FIG. 2B is a highly schematic transverse cross-section through a sealing ring of FIG. 2A.

DETAILED DESCRIPTION

As used herein, the term "inflow end," when used in connection with a prosthetic heart valve, refers to the end of the heart valve through which blood enters when the valve is functioning as intended. The term "outflow end," when used in connection with a prosthetic heart valve, refers to the end of the heart valve through which blood exits when the valve is functioning as intended. As used herein, the terms "generally," "substantially," and "about" are intended to mean that slight deviations from absolute are included within the scope of the term so modified. Like numbers refer to similar or identical elements throughout. When used herein in the context of a prosthetic heart valve, or a component thereof, the lengthwise or axial direction refers to the direction along a longitudinal axis passing through the center of the stent or heart valve in the direction of blood flow. When used herein in the context of a prosthetic heart valve, or a component thereof, the circumferential direction refers to the direction along the circumference of the prosthetic heart valve and about its longitudinal axis. When used herein in the context of a prosthetic heart valve, or a component thereof, the radial direction refers a direction orthogonal to the longitudinal axis of the component (or otherwise to a direction having a component that is orthogonal to the longitudinal axis).

Figure 1:
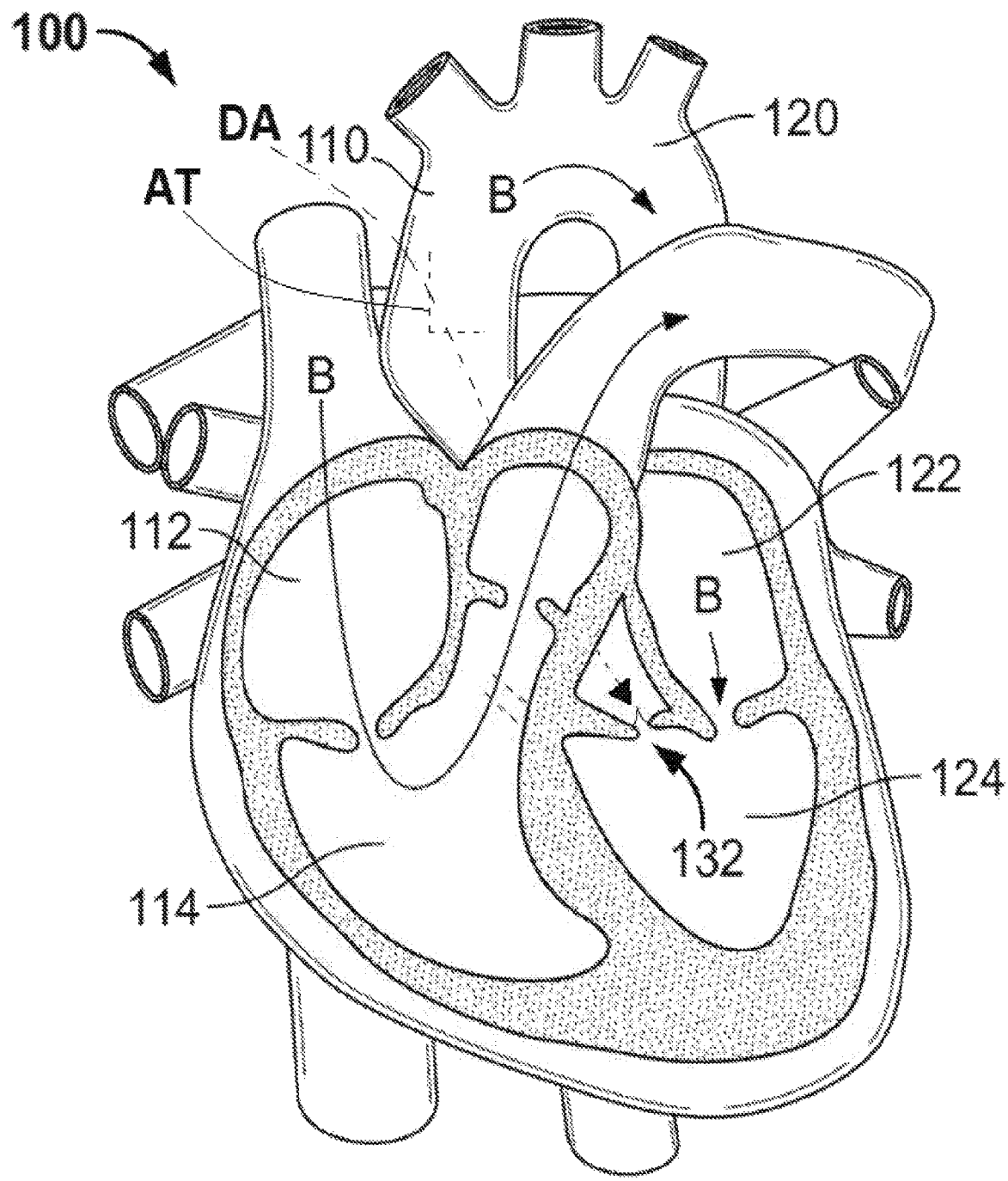
FIG. 1 is a highly schematic cutaway representation of a human heart showing a surgical delivery approach.

FIG. 1 is a highly schematic cutaway representation of human heart 100. The human heart includes two atria and two ventricles: right atrium 112 and left atrium 122, and right ventricle 114 and left ventricle 124. Heart 100 further includes aorta 110 and aortic arch 120. Disposed between left ventricle 124 and aorta 110 is aortic valve 132. Aortic valve 132 is generally a three-leaflet valve that opens as a result of increased pressure in left ventricle 124 as it fills with blood. As ventricular pressure increases above that of aorta 110, aortic valve 132 opens and blood passes into aorta 110. Blood flows through heart 100 in the direction shown by arrows "B".

A dashed arrow, labeled "DA," indicates a direct aortic approach (or "surgical approach") for implanting a prosthetic heart valve, in this case to replace aortic valve 132. In the surgical approach, an incision, such as an "L"-shaped aortotomy AT, is made in the aorta 110. The prosthetic heart valve is generally coupled to a valve holder held by the surgeon, and the valve is manually inserted through the aortotomy AT and maneuvered to the site of implantation at aortic valve 132. Other types of aortic incisions may also be appropriate, such as a transverse incision. This is essentially a planar cut made at about 90 degrees to the longitudinal axis of the aorta and about two-thirds of the way through the circumference of the aorta. Such methods may provide direct visualization of the implantation. During the procedure, the patient may be placed on cardiopulmonary bypass. As noted above, although a prosthetic heart valve may be sutured in place, using a sutureless prosthetic valve may provide for easier and faster placement, reducing the time the patient is kept on bypass.

While surgical valves may be held in the desired position and orientation via sutures coupling the valve to the native anatomy, both sutureless valves and transcatheter valves may benefit from features that anchor the valve within the native valve annulus. For example, hooks, barbs, or other structures may be coupled to the prosthetic heart valve to help maintain the position of the prosthetic heart valve in the native valve annulus, for example by hooking over a native heart valve leaflet.

After implantation, imperfect sealing between the prosthetic heart valve and the site of implantation may cause complications such as paravalvular leakage (also known as perivalvular leak or "PV leak"), or blood flowing through a channel between the structure of the implanted valve and cardiac tissue as a result of the imperfect sealing. The prosthetic heart valve may be provided with additional structures, some of which are described in greater detail below, that provide enhanced sealing between the prosthetic heart valve and the native valve annulus to minimize or prevent PV leak. Certain PV leak mitigation features may provide an anchoring function in addition to the sealing function.

In some patients, the native aortic valve 132 may have a diseased state which provides effective surfaces for anchoring. For example, a patient may have a native aortic valve 132 with thickened leaflets and/or calcific nodules on the leaflets. These diseased leaflets may provide a substrate suitable for anchoring a prosthetic heart valve. For example, a prosthetic heart valve with hooks that hook over the diseased leaflet may provide suitable anchoring force to keep the prosthetic heart valve from migrating. However, in other patient subsets, such as those with aortic insufficiency caused by aging or rheumatic fever, the native leaflets of aortic valve 132 may not provide a suitable substrate for anchoring. Further, the leaflets of native aortic valve 132 may be partially or completely resected during the procedure of implanting the prosthetic heart valve. This may result in similar problems as are encountered in patients with aortic insufficiency in that it is more difficult to suitably anchor a prosthetic heart valve in a patient with partially or fully resected leaflets. For example, an anchor feature that typically hooks over a native leaflet may be ineffective in anchoring when the native leaflets are partially or completely resected.

FIG. 2A illustrates a sutureless heart valve 200 according to one embodiment of the disclosure intended to reduce the likelihood and severity of PV leak between the heart valve and the native valve annulus and to provide effective anchoring in a variety of patient anatomies. Heart valve 200 may have a stent 202 which extends between inflow end 230 and outflow end 232, and a valve assembly 240 including a plurality of leaflets 208 and a cuff 206.

Stent 202 may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, titanium, nickel, stainless steel, and alloys thereof, including nitinol. Other metals that have elastic and/or memory properties may also be suitable, such as spring stainless steel, tradenamed alloys such as Elgiloy® and Hastelloy®, CoCrNi alloys (e.g., tradename Phynox), MP35N®, CoCrMo alloys, mixtures of such alloys or mixtures of metal and polymer fibers. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. It should be understood that stent 202 may be collapsible and expandable. This capability may allow prosthetic heart valve 200 to be delivered via a transcatheter approach while in a collapsed condition. Prosthetic heart valve 200 may also be delivered via a surgical approach without the use of sutures. Because stent 202 may tend to transition to the expanded condition in the absence of an applied restraining force, prosthetic heart valve 200 may be secured after implantation, at least in part, by radial force.

Furthermore, stent 202 need not be cylindrically shaped. For example, stent 202 may take the shape of an ellipse or other shapes, such as a general "D" shape with a substantially straight section and an arcuate section extending from one side of the straight section to the other. Such a "D" shape may better conform to particular anatomies, such as the mitral valve, the tricuspid valve, or a diseased bicuspid valve. Other portions of the valve, such as the sealing rings 250A, 250B, described in greater detail below, may take similar shapes including a general "D" shape, for example, depending on the stent 202 on which they are positioned.

Valve assembly 240 may be wholly or partly formed of any suitable biological material or polymer. Examples of biological materials suitable for valve assembly 240 include, but are not limited to, porcine or bovine pericardial tissue. Examples of polymers suitable for valve assembly 240 include, but are not limited to, polyurethane, silicone, PTFE, and polyester. In at least some examples, portions of valve assembly 240, including the cuff 206 and the suture used, may include an ultra-high molecular weight polyethylene. Although valve assembly 240 typically includes one or more leaflets, other suitable valve assemblies without leaflets that work as one-way valves may be alternatively used.

It should be noted that while the disclosure herein is predominantly directed to a prosthetic tricuspid valve, i.e., a valve having three distinct mutually coapting leaflets, and a stent having a shape as illustrated in FIG. 2A, the valve and stent may take other forms. For example, the valve could be a bicuspid valve, i.e., a valve having two coapting leaflets, or other types of valves, including valves with a greater or lesser number of leaflets as well as non-leaflet valves. Similarly, stent 202 could have different shapes, such as a flared or conical annulus section, a more or less bulbous aortic section, a differently shaped transition section between the aortic section and the annulus section, or any other suitable shape, and may or may not be collapsible.

Heart valve 200 may include a pair of sealing elements, such as a sub-annular sealing ring 250A at or near inflow end 230 of stent 202, and a supra-annular sealing ring 250B disposed closer to outflow end 232 than sub-annular sealing ring 250A. The pair or sealing elements may help mitigate PV leak while simultaneously providing suitable anchoring force to anchor heart valve 200 in patients with various types of native anatomy. FIG. 2B illustrates an enlarged cross-sectional view of sealing ring 250A taken along a cutting plane P transverse to the circumferential direction of sealing ring 250A. Sealing ring 250B may take a similar or identical form as sealing ring 250A, with the main or only difference being the position of sealing ring 250B with respect to stent 202. As such, unless explicitly noted otherwise herein, sealing ring 250B should be understood to be identical to sealing ring 250A other than its position relative to stent 202.

Generally, sealing ring 250A may comprise tube 260A with or without covering 270A, with optional outer filler 280A between covering 270A and tube 260A, and with optional inner filler 290A inside tube 260A. Unless stated otherwise, the term filler, as used herein, refers to outer filler 280A and/or inner filler 290A. Sealing ring 250A may include any combination of tube 260A, covering 270A, and filler. If outer filler 280A is used, covering 270A may be used to contain outer filler 280A within sealing ring 250A. Prior to describing sealing rings 250A and 250B in greater detail, the function of sealing rings 250A and 250B is briefly explained.

Figure 2C:
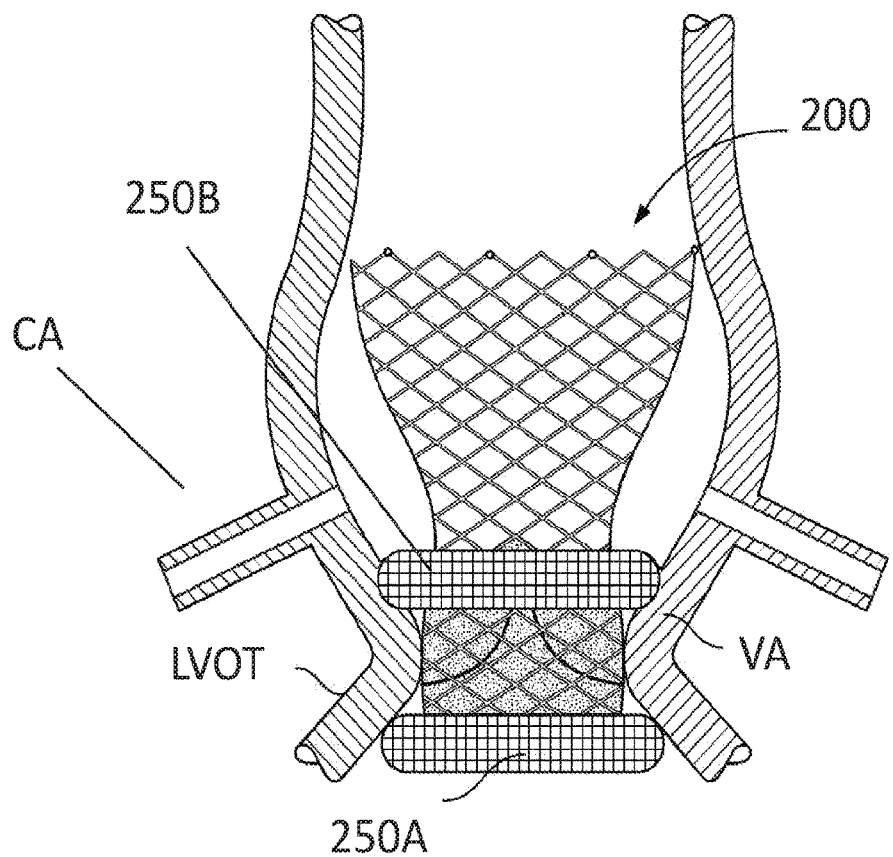
FIGS. 2C-D are highly schematic side views of the heart valve of FIG. 2A implanted into a native valve annulus with resected native valve leaflets.
Figure 2D:
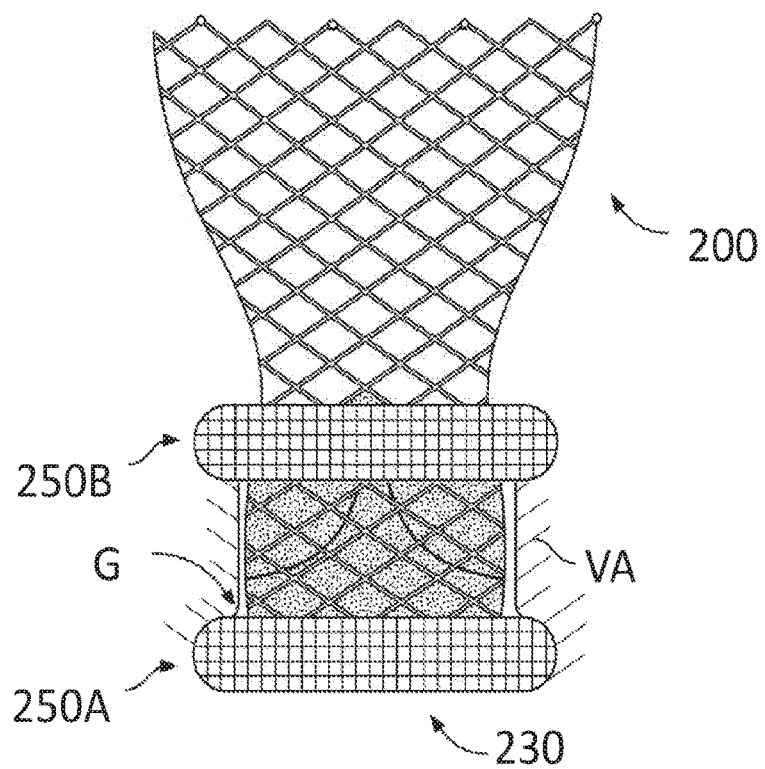

FIGS. 2C-D illustrate prosthetic heart valve 200 disposed within a native valve annulus VA from which the native valve leaflets have been resected. When implanted within native valve annulus VA, sealing ring 250A may be disposed, for example, below native valve annulus VA (i.e., in a sub-annular position). Sealing ring 250B may be disposed, for example, above native valve annulus VA (i.e., in a supra-annular position). As shown in FIG. 2C, sealing ring 250A is disposed such that it is in contact with the left ventricular outflow tract LVOT, while sealing ring 250B is disposed between native valve annulus VA and coronary arteries CA. Such positioning helps to provide a seal between prosthetic heart valve 200 and the native heart tissue. For example, as illustrated in FIG. 2D, despite gaps G between heart valve 200 and native valve annulus VA, sealing rings 250A and 250B help prevent retrograde blood flow around the outer circumference of valve 200.

The positioning of sealing rings 250A and 250B also provides robust anchoring on both sides of native valve annulus VA. In particular, when prosthetic heart valve 200 is implanted in the native aortic valve annulus VA, sealing ring 250A helps prevent heart valve 200 from migrating into aorta 110 while sealing ring 250B helps prevent heart valve 200 from migrating into left ventricle 124. The presence of both sub-annular sealing ring 250A and supra-annular sealing ring 250B to anchor prosthetic heart valve 200 on both sides of native valve annuls VA may provide robust anchoring in a variety of patient populations, regardless of native valve anatomy. For example, prosthetic heart valve 200 may provide anchoring in patients that have their native aortic valve leaflets partially or fully resected, as well as in patients with conditions such as aortic insufficiency in which the native aortic valve leaflets are not resected but provide suboptimal substrate quality for anchoring. For example, in a patient that does not have the native valve leaflets resected, spacing the sub-annular sealing ring 250A and supra-annular sealing ring 250B between about 15 mm and about 20 mm apart may provide robust anchoring. In patients with partially resected native leaflets, that spacing may be between about 5 mm and about 15 mm, while in patients with fully resected leaflets may benefit from spacing of between about 2 mm and about 5 mm between sub-annular sealing ring 250A and supra-annular sealing ring 250B. However, it should be understood that the dimensions provided above are merely exemplary, and other dimensions may be suitable depending on the particular anatomy of a patient.

As noted above, sealing ring 250A may include elements such as tube 260A, covering 270A, and filler. Sealing ring 250B may include similar or identical components. Generally, tube 260A may provide a structural support onto which covering 270A may be attached and into which outer filler 280A and/or inner filler 290A may be inserted. Tube 260A alone may provide sealing and anchoring of prosthetic valve 200, although such functions may be enhanced with the addition of covering 270A and/or filler.

Tube 260A of sealing ring 250A may be formed of various materials, including any of those used to form stent 202, and may have one or more of a variety of structures. For example, the material of tube 260A may be individual strands braided into a generally tubular mesh structure, or may be an individual strand wound into a coil. For a braided tube 260A, the strands forming the braid may have a particular relative orientation with respect to one another (e.g., a helical braid).

Covering 270A may be formed of one or more materials having low permeability or no permeability to fluids, such as water and/or blood. For example, covering 270A may be formed of tissue, including but not limited to pericardium or other sheet-like tissue obtained from animals or by tissue engineering. The covering 270A may be formed of a fabric-type material, such as a fabric formed of polytetrafluoroethylene (PTFE), polyethylene terephthalate (PET), or ultra-high molecular weight polyethylene (UHMWPE). The covering 270A may also be formed of synthetic or natural polymers, such as silicones, polyvinyl alcohol (PVA), or collagen sheets. The covering 270A may be formed of any one or any combination of the above-listed materials.

The filler may be formed of any of a variety of materials. For example, the filler may be composed of any of the materials used to form tube 260A, such as a coil or mesh braid formed of Nitinol. The filler may also be composed of any of the materials used to form covering 270A, such as fabrics, tissues, and synthetic or natural polymers. Furthermore, the filler may be composed of a water swellable material, such as natural sea sponge, swellable beads formed of, for example, PVA microspheres that expand upon contact with blood, or other materials that expand upon exposure to body conditions. Other materials that expand upon exposure to temperatures found in the body or to components of the blood may also be suitable for the filler. Another potential material for the filler is a highly compressible sponge, for example one made from alginate cross-linked at low temperatures. Such a highly compressible sponge may collapse to a large extent when shear forces are applied, while being able to return to its original shape upon removal of the forces. Further, a single filler composed of a single material or a combination of materials described above may be used, or multiple fillers each composed of one or a combination of any of the above materials may be used. For example, outer filler 280A may be formed of a first material while inner filler 290A may be formed of a second material. Alternatively, a homogenous mixture of different materials may be used for outer filler 280A and/or inner filler 290A. Further, fillers of different materials may be positioned in different sections of sealing ring 250A, or fillers may be provided as layers of different materials.

In one embodiment, prosthetic heart valve 200 may include sealing ring 250A that includes tube 260A formed of a braided mesh of a shape-memory material, of a super-elastic material, of a bio-compatible polymer, or of another material, including those that are capable of being collapsed and expanded into a desired shape. Generally, tube 260A may take the shape of a hollow torus wrapped around a portion of stent 202. It should be understood that tube 260A need not meet the precise mathematical definition of a torus or other toroid. Tube 260A may comprise a braided metal fabric that is both resilient and capable of heat treatment to substantially set a desired shape, such as Nitinol, or any other metal described above that is suitable for forming stent 202. However, it should be understood that other materials, such as braided polymers, including polypropylene, may be used for the braided mesh version of tube 260A. Depending on the individual material selected, the strand diameter, number of strands per area or strand density, and pitch may be altered to achieve the desired properties for tube 260A. If sealing ring 250A comprises only braided mesh, the braided tube 260A may help in reducing PV leak, for example by creating a seal as blood clots form in the braid. PV leak may be further mitigated to the extent tissue in-growth occurs on sealing ring 250A, such as by endothelialization and/or epithelialization. Such sealing by clotting and/or thrombus formation may take up to an hour or more to form, with tissue in-growth occurring over a longer time. However, faster sealing may be desirable. For example, rapid sealing may provide a physician with immediate or near immediate feedback that PV leak is not occurring at unacceptable levels. Covering 270A and/or filler may be used in combination with braided tube 260A (or a coiled tube 260A as described below) to accelerate sealing and enhance tissue in-growth.

One of the advantages of using braided Nitinol for tube 260A is that the structure relatively easily undergoes a transition into different shapes. This may provide benefits for delivery via a transcatheter approach or a surgical approach. For example, it may be easily collapsible for delivery, easily expandable upon implantation, and may change shape as appropriate to fill in gaps G in native annulus VA. However, as noted above, it may be desirable to add a covering 270A and/or filler if tube 260A is formed of braided mesh. The addition of such material may change the way the braided mesh changes shapes. In particular, if the braid is covered tightly with a covering 270A, the braid may not expand as freely as it would without such a covering. One possible solution to this challenge is choosing a flexible material for covering 270A, as well as loosely attaching covering 270A to tube 260A. For example, sutures may be used to form tacking stitches or expandable stitches to couple covering 270A to tube 260A. Another possible solution is to use a different structure for tube 260A. However, when prosthetic heart valve 200 is implanted using a surgical approach, the ability of tube 260A to change shape may be less important than when implantation is accomplished using a transcatheter approach.

Instead of forming tube 260A of a braided mesh, it may be desirable to form tube 260A from a coiled material, such as coiled Nitinol (or any other material suitable for use in forming stent 202). In particular, tube 260A may be formed of a single strand or wire of material, or single stands or wires of material attached end-to-end, coiled into a desired shape. For example, tube 260A may be formed of a strand or wire of Nitinol coiled into a circular shape, a rectangular shape, or a diamond shape. The strands of material forming the coil may have various cross-sectional shapes, such as round, flat (e.g., a ribbon), rectangular, or others, all of which are referred to hereafter as "wires." Still further, one or more wires may be wound into a coil having parallel windings, multiple wires may be wound together in different directions (e.g., to form a braid), or two or more wires may be wound together in the same direction (e.g., two or more wires wound as a double helix). In addition, the coil need not be a closed coil, but may be an open coil having, for example, a "U" or "C" shape.

Generally, tube 260A may have different qualities when formed from a coil compared to those exhibited by a braided mesh. For example, a tube 260A formed from a coil may collapse to a smaller profile than a similar tube formed of a braided mesh. On the other hand, if sealing ring 250A is formed solely of a tube 260A comprising a coil, sealing via clotting may be slower than with the braided mesh version, or may never occur at all. But when covering 270A and/or filler is included with a tube 260A formed of a coil, sealing ring 250A may seal against PV leak rapidly. However, it should be clear that a covering 270A and/or filler may similarly be used in conjunction with a braided mesh version of tube 260A, in which case the sealing quality may be similar to that achieved when a covering 270A and/or filler is used with a coiled version of tube 260A.

Figure 2E:
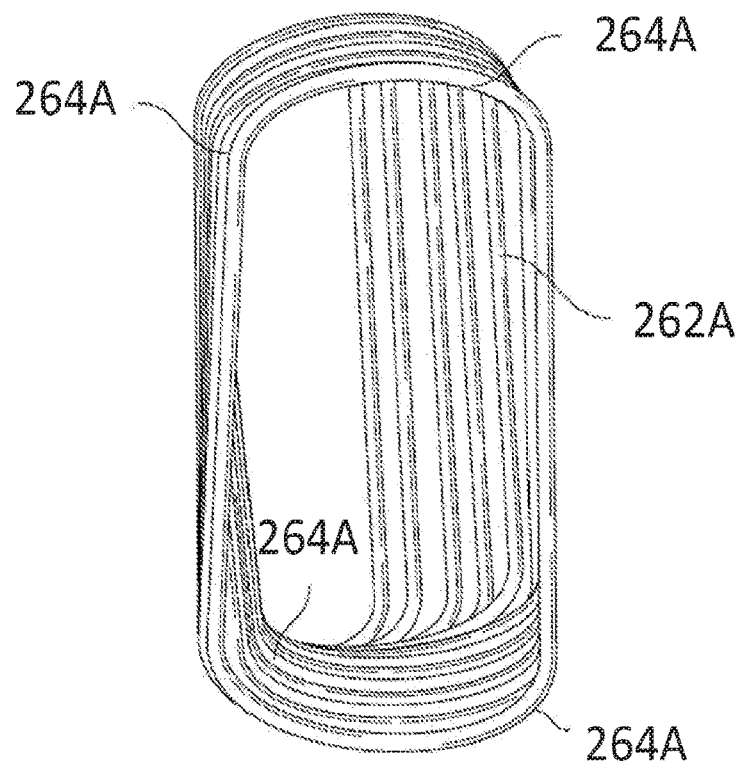
FIG. 2E is a front view of a rectangular coil of a sealing ring.
Figure 2F:
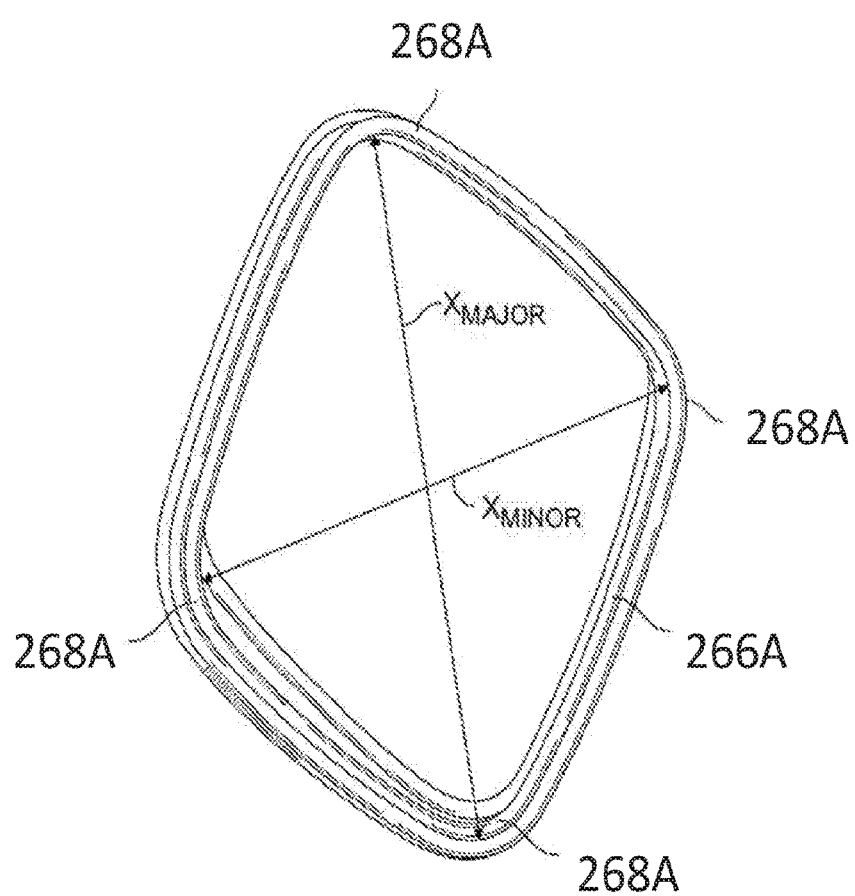
FIG. 2F is a front view of a diamond coil of a sealing ring.

As noted above, when tube 260A is formed of a coil, the coil may take different general shapes, such as that of a circle (not illustrated), of a rectangle (FIG. 2E), or of a diamond (FIG. 2F). The coils shown in FIGS. 2E-F are viewed along the same cutting plane P shown in FIG. 2B. As such, multiple turns or iterations of each coil shape are visible in FIGS. 2E-F. Stated more precisely, the shape of each individual turn of the coils shown is a rectangle (FIG. 2E) or a diamond (FIG. 2F). As will become apparent from the description below, the shape of the coil may provide certain advantages, depending on the techniques used to implant the prosthetic heart valve.

Prosthetic heart valve 200 may alternatively be delivered via a transcatheter approach in which the prosthetic heart valve is collapsed, loaded into a delivery catheter, and delivered to the site of implantation. The shapes of the coil forming tube 260A described above may be advantageous for a transcatheter delivery technique because, for example, the corners 264A of rectangular coil 262A and the peaks 268A of diamond coil 266A facilitate the collapse of the respective coils during loading, delivery, and/or resheathing of valve 200.

It should be noted that rectangular coil 262A is shown in FIG. 2E (and diamond coil 266A in FIG. 2F) not in the form of tube 260A, but rather a segment thereof. In stent 202, rectangular coil 262A or diamond coil 266A would extend along a circumferential path around inflow end 230 of valve 200, forming tube 260A. As should be clear from the above, the term "tube" does not solely refer to an elongated cylindrical structure, as the rectangular coil 262A and diamond coil 266A extending circumferentially around stent 202 is still considered herein as a tube 260A. In fact, although shown throughout this disclosure as a torus, the tube 260A need not be a toroid at all. For example, tube 260A of sealing ring 250A may undulate such that points on its proximal (or distal) surface do not lie in the same plane as other points on its proximal (or distal) surface. As such, sealing ring 250A may have an undulating quality as well.

Varying the geometric of the shape of the coil may provide for different effects in terms of profile and sealing. For example, when using a diamond coil 268A, the lengths of the major axis $X_{MAJOR}$ and minor axis $X_{MINOR}$ may be, respectively, approximately 3 mm and approximately 2 mm, approximately 4 mm and approximately 2 mm, or approximately 4 mm and approximately 3 mm. These lengths of the major and minor axes should be understood to be examples, and not requirements. The examples given above may be useful for achieving a bulge in sealing ring 250A of between about 2 mm and about 5 mm from the outer circumference of the stent 202, which may be particularly effective at reducing PV leak. In other words, if diamond coil 268 is coupled to stent 202 at one of the two vertices defining the minor axis $X_{MINOR}$, the bulge formed will be approximately the length of minor axis $X_{MINOR}$. However, coil 268A may be attached at other locations so that the bulge is any size between $X_{MINOR}$ and $X_{MAJOR}$. Further, as noted above, wires having cross-sections other than circular, including flat and/or rectangular, may be used to form coil tube 260A. While the thickness of the wire forming the coil of tube 260A may vary, one exemplary range of thicknesses is between about 0.05 mm and about 0.175 mm. Where the wire has a circular cross-section, the thickness of the wire will be equal to its diameter. Where the wire has a rectangular cross-section, the thickness of the wire will be equal to its width. It should be noted that the above dimensions provided in relation to components of tube 260A, as well as any other dimensions provided herein, are for illustrative purposes. Different dimensions may be used without departing from the scope of this disclosure.

Other features of the braids and/or coils forming tube 260A may be modified and optimized to achieve a better seal against PV leak, including, for example, the coil or braid density, shape, and stiffness. Also, when tube 260A is formed of a coiled wire, the ratio of the thickness of the wire to the spacing between adjacent iterative windings of the coil (i.e., pitch) may have an effect on PV leak sealing. For example, a relatively large ratio of wire thickness to pitch may lead to kinking or tenting (i.e., a deviation from a smooth circumference) in the tube 260A, which may reduce the effectiveness of sealing against PV leak. In some embodiments, it may be preferable that the ratio of wire thickness to the pitch be between approximately 1:6 and approximately 1:32.

Although sealing rings 250A and 250B are described above as being substantially similar or identical, certain differences may enhance the performance of prosthetic heart valve 200. For example, it may be desirable for supra-annular coil 250B to exert greater radial force than sub-annular coil 250A to withstand higher forces due to back-flow pressure of blood in aorta 110. On the other hand, it may be desirable for sub-annular coil 250A to exert less radial force in order to avoid mitral valve impingement. In sealing rings incorporating a tube formed from a coiled wire, the greater the thickness of the wire, the greater the radial force exerted by the tube will be. Thus, when sealing rings 250A and 250B include tubes formed from a coiled wire, the wire forming the coil of the tube may be thicker for supra-annular sealing ring 250B than for sub-annular sealing ring 250A. For example, while the wire forming the coiled tube 260A of sub-annular sealing ring 250A may have a thickness between about 0.05 mm and about 0.175 mm, the thickness of the wire forming the coiled tube of supra-annular sealing ring 250B may be between about 1.5 and about 2 times greater, or between about 0.075 mm and about 0.350 mm. It should be understood that other dimensions of the coiled tube may be manipulated to alter the radial force, including cross-sectional dimensions of the wire forming the coiled tube, the pitch and/or spacing of the coil, the shape of each turn of the coil, and material choice and/or processing of the material of the wire forming the coil. Still further, due to the positioning of supra-annular sealing ring 250B near the coronary arteries CA, it may be important to size the supra-annular sealing ring to avoid occluding the coronary arteries CA.

Figure 3A:
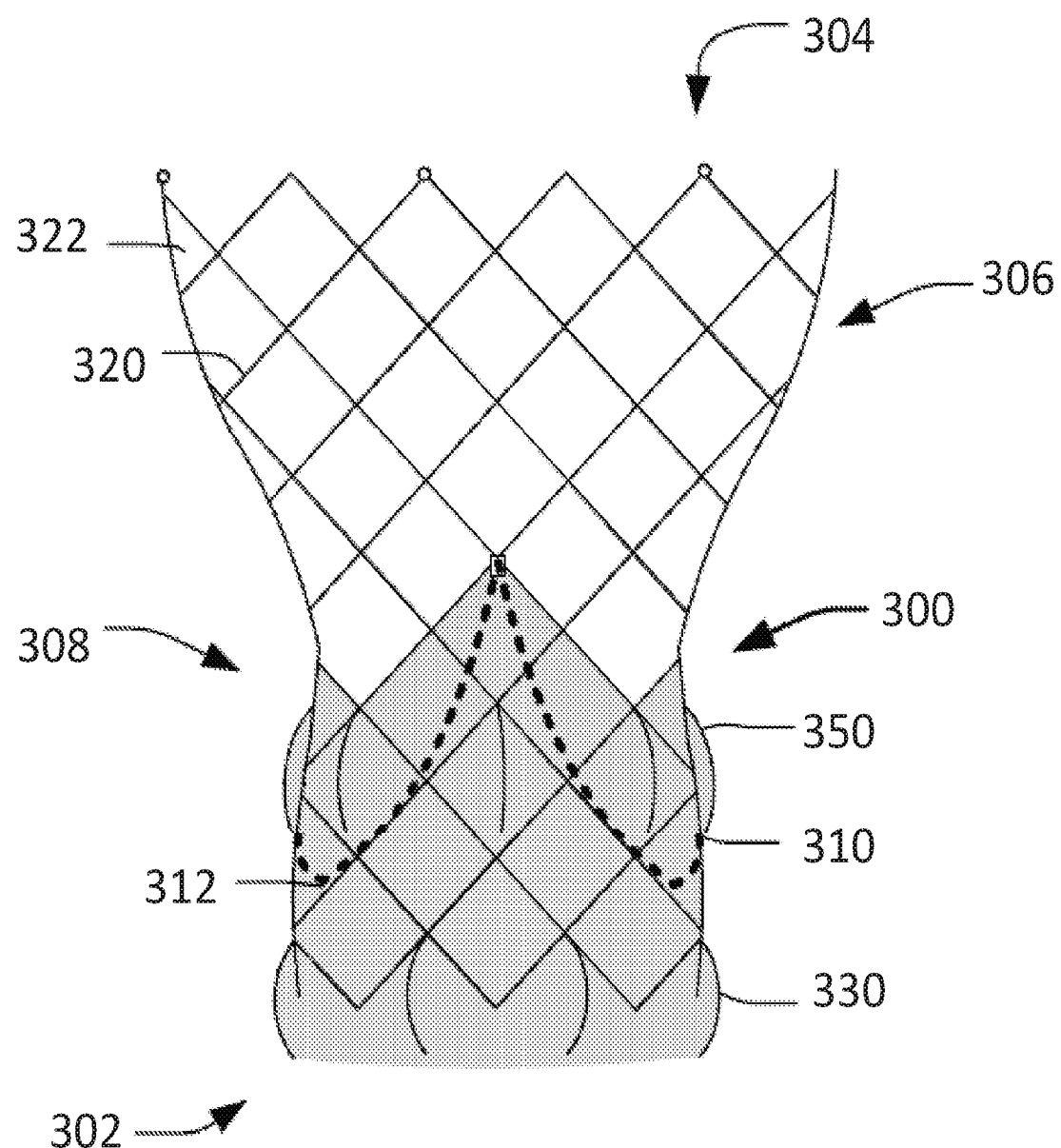
FIG. 3A is a highly schematic side view of one embodiment of a heart valve having bowed runners.

FIG. 3A illustrates a heart valve 300 according to another embodiment intended to provide robust anchoring on each side of a native heart valve, such as native aortic valve 132, while also reducing the occurrence of PV leak. Heart valve 300 extends between inflow end 302 and outflow end 304, and may generally include stent 306 and valve assembly 308 having a plurality of leaflets 310 and cuff 312. Heart valve 300 may be formed of any of the materials and in any of the configurations for forming heart valve 200 as described above.

Stent 306 may include a plurality of struts 320. Struts 320 may come together to form cells 322 connected to one another in one or more annular rows around the stent. Connected to struts 320 are a plurality of sub-annular runners 330 and supra-annular runners 350, which are additional struts that bow or bulge out radially when stent 306 is in a relaxed condition, as is described in greater detail with reference to FIGS. 3B and 3C.

Figure 3B:
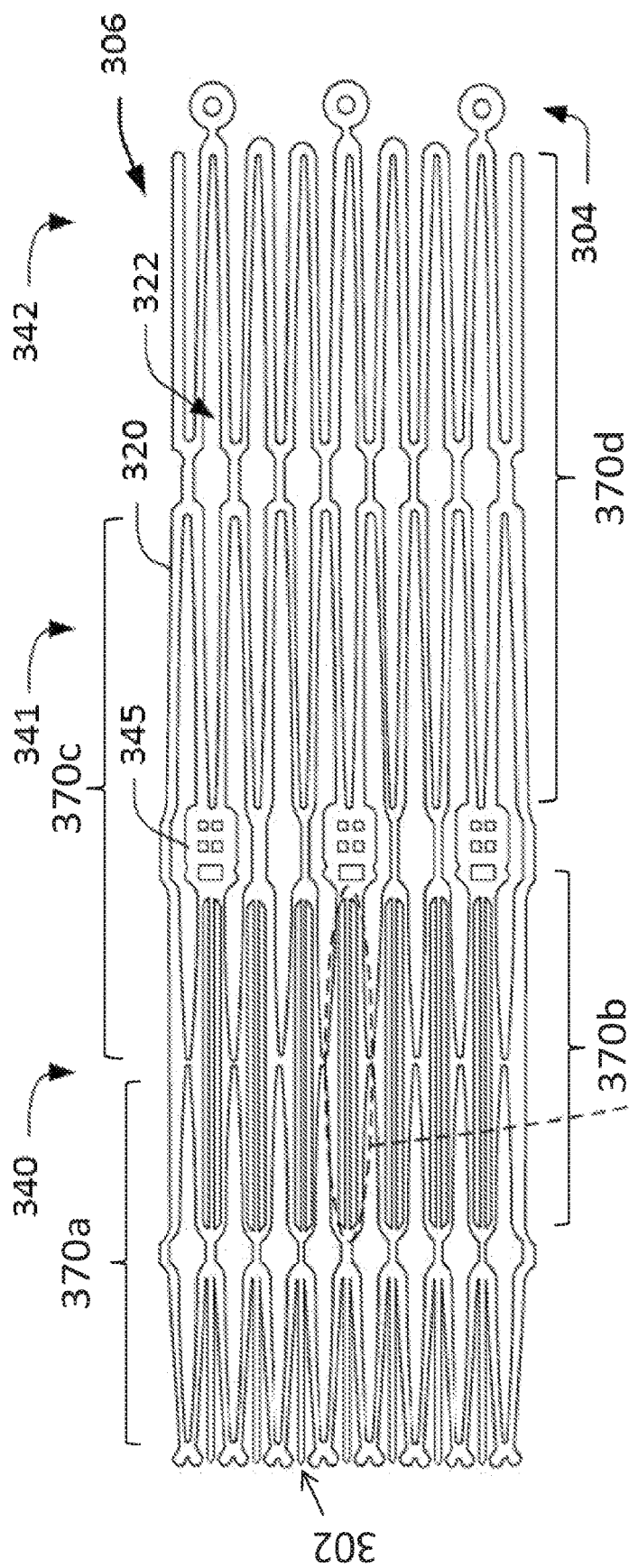
FIG. 3B is a developed view of the stent of the heart valve of FIG. 3A in the collapsed configuration.

In order to better appreciate the attachment and placement of supra-annular runners 350, stent 306 is shown in FIG. 3B in a collapsed and flattened condition (i.e., as if the stent had been cut longitudinally and flattened to a single layer thickness). It should be understood that although stent 306 may be collapsible and expandable, the method of delivery of prosthetic heart valve 300 is not limited to transcatheter delivery, but may alternatively be delivered via a surgical approach while in a partially or fully expanded condition, as described in greater detail in connection with FIGS. 4A-D. For the sake of clarity, valve assembly 308 is not shown in FIG. 3B. In the illustrated embodiment, stent 306 includes four annular rows of cells 370a-d extending from inflow end 302 to outflow end 304. In the collapsed configuration of stent 306, each of cells 322 is also collapsed. Stent 306 extends from inflow or annulus end 302 of heart valve 300 to outflow or aortic end 304, and includes annulus section 340 adjacent inflow end 302, aortic section 342 adjacent outflow end 304, and transition section 341 between annulus section 340 and aortic section 342. Commissure attachment features 345 may be positioned entirely within annulus section 340 or at the juncture of annulus section 340 and transition section 341.

Figure 3C:
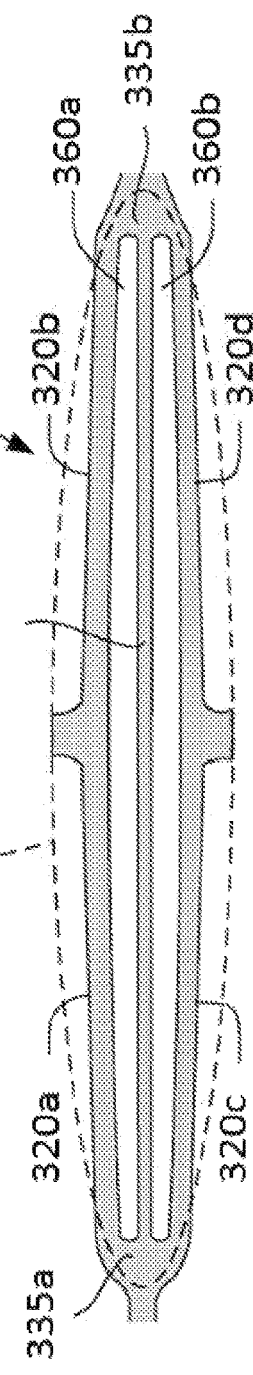
FIGS. 3C and 3D are enlarged highly schematic partial plan views of a stent cell having a supra-annular runner in the collapsed configuration and bowed configuration, respectively.
Figure 3D:
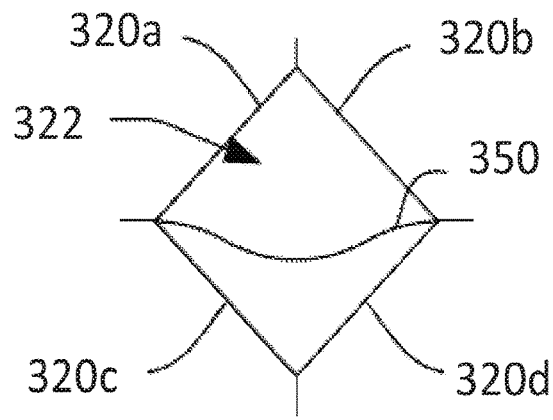

One or more cells 322 in the second annular row of cells 370b may include supra-annular runners 350 nested therein. An enlarged partial plan view of cell 322 including a supra-annular runner 350 is shown in FIG. 3C. Four struts 320a, 320b, 320c, 320d may join to form cell 322, each strut being attached to two adjacent struts. In the collapsed configuration of stent 306, cell 322 may be stadium-shaped as shown. In the expanded configuration of stent 306, cell 322 may shorten in the length direction of stent 306 between inflow end 302 and outflow end 304, and struts 320 may generally form a diamond shape (FIG. 3D).

Supra-annular runners 350 may extend across cell 322 from first attachment end 335a where struts 320a and 320c meet to second attachment end 335b where struts 320b and 320d meet, and may be affixed to stent 306 by welding, adhesive, or any other suitable technique known in the art. Rather than being separately formed and affixed to stent 306 at attachment ends 335a and 335b, runners 350 may be integrally formed with stent 306, such as by laser cutting both stent 306 and runners 350 from the same tube. Runners 350 may be formed of a shape memory material such as those described above for forming stent 202 of FIG. 2A, and may have a substantially linear configuration in the collapsed configuration of heart valve 300 (FIG. 3C) and a curved or bowed configuration in the expanded configuration of heart valve 300 (FIG. 3D).

In the collapsed configuration, runner 350 may bisect cell 322 into first portion 360a and second portion 360b. As the length of cell 322 shortens in the expanded configuration of heart valve 300, i.e., as attachment ends 355a and 355b move closer to one another, runner 350 bows or deflects outwardly of the surface defined by struts 320a, 320b, 320c, and 320d. Stent 306 may also be heat set such that struts 320 and runner 350 return to a predetermined shape in the fully expanded or relaxed configuration (e.g., when no external forces are applied thereto). When cuff 312 (FIG. 3A) is coupled to the abluminal surface of annulus section 340 of stent 306, the cuff is substantially tubular when runners 350 are not bowed outwardly. When runners 350 bow outwardly on the expansion of heart valve 300, they form protuberances in cuff 312 to help anchor and seal heart valve 300 within the native valve annulus VA. In one example, the runners 350 may bow outwardly between about 3 mm and about 5 mm, with the length of runners 350 being between about 8 mm and about 10 mm. However, these dimensions are merely exemplary and other dimensions may be suitable.

Figure 3E:
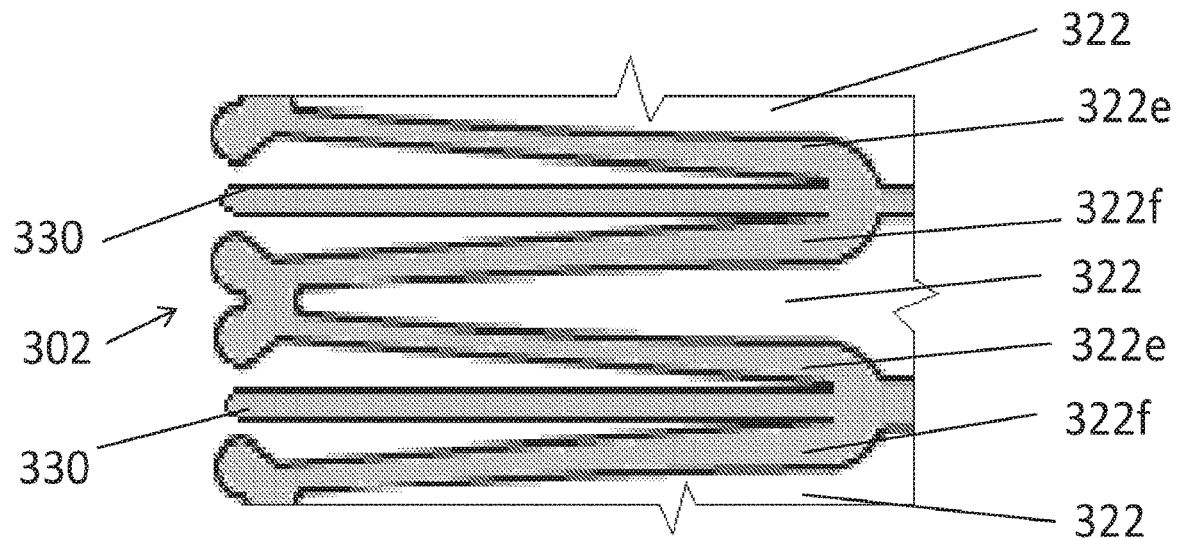
FIGS. 3E and 3F are enlarged highly schematic partial plan views of a stent cell having a sub-annular runner in the collapsed configuration and bowed configuration, respectively.
Figure 3F:
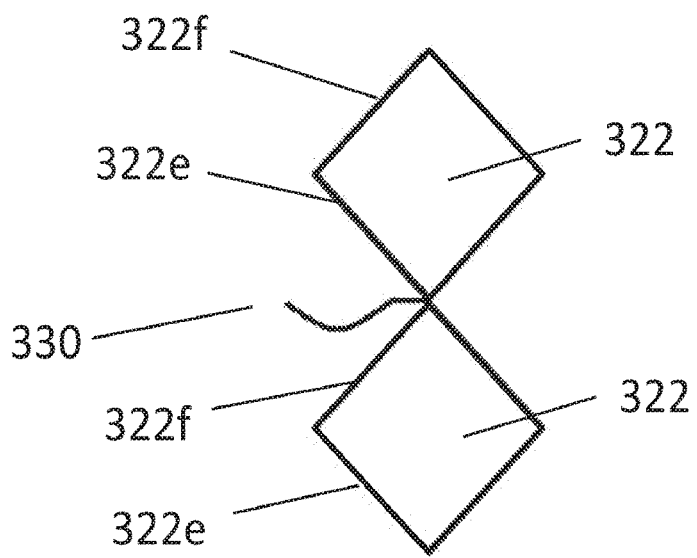

In order to better appreciate the attachment and placement of sub-annular runners 330, FIG. 3E shows an enlarged partial plan view of the inflow end 302 of stent 306 in the collapsed condition. In the collapsed configuration of stent 306, each of cells 322 is also collapsed. Each cell 322 in the first annular row of cells 370a positioned nearest the inflow end 302 of stent 306 may include four struts that join to form cell 322, with two of the four struts 320e and 320f shown in FIG. 3E. Runners 330 may be positioned in the space between adjacent cells 322 at the inflow end 302 of stent 306. In other words, each runner 330 is positioned in the space between strut 322f of one cell 322 in the first row 370a and strut 322e of an adjacent cell 322 in the first row. More particularly, each runner 330 has a first end joined to stent 306 at the juncture of strut 322e of one cell 322 and strut 322e of an adjacent cell 322, and a second free end extending toward inflow end 302 of the stent. As with supra-annular runners 350, sub-annular runners 330 may be affixed to stent 306 or integrally formed with the stent. Runners 330 may also be formed of a shape memory material such as those described above for forming stent 202 of FIG. 2A, and may have a substantially linear configuration in the collapsed configuration of heart valve 300 (FIG. 3E) and a curved or bowed configuration in the expanded configuration of heart valve 300 (FIG. 3F).

Figure 3G:
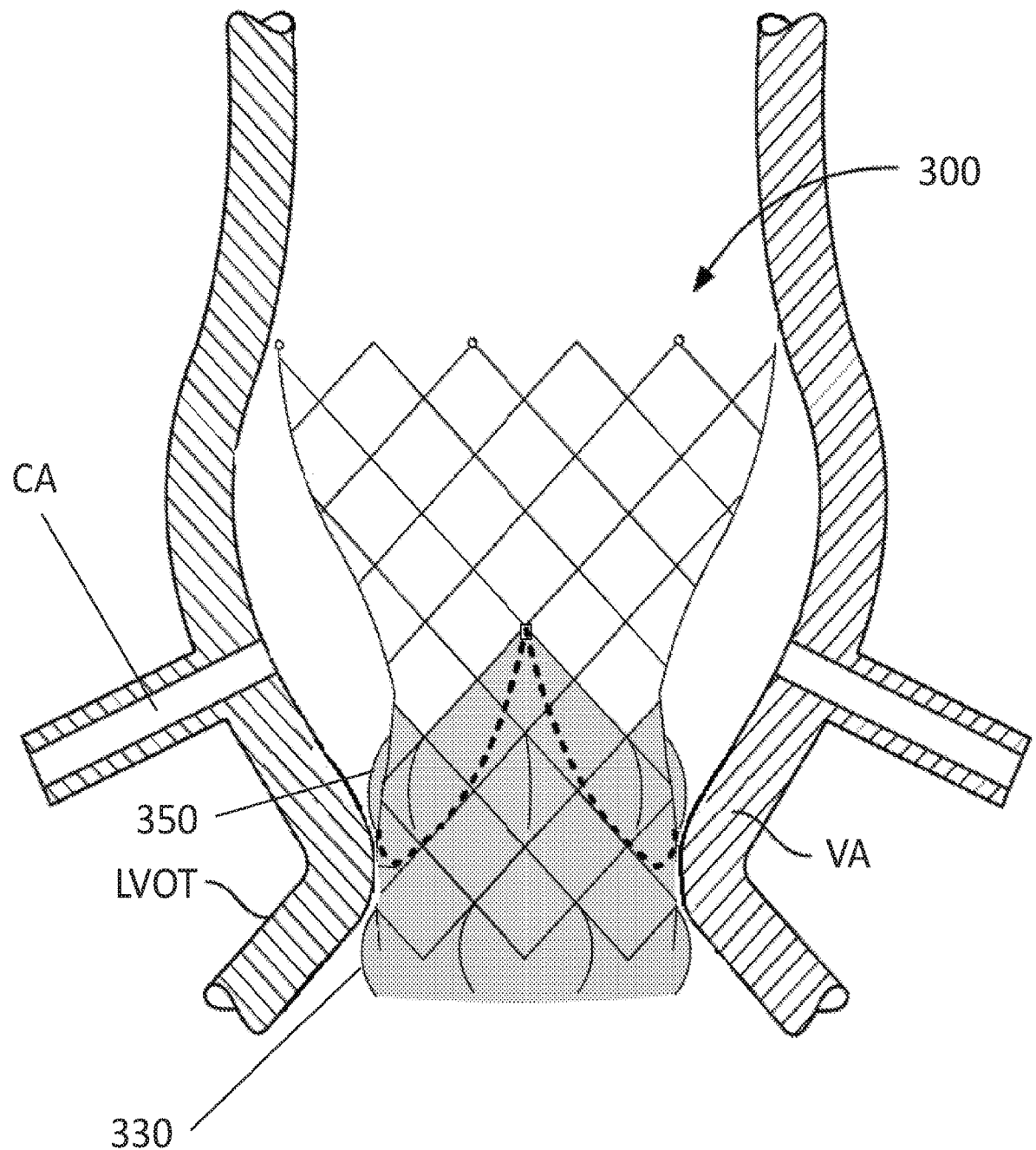
FIG. 3G is a highly schematic side view of the heart valve of FIG. 3A implanted into a native valve annulus with resected native valve leaflets.

As described above, sub-annular runners 330 are attached to stent 302 at only one end. While supra-annular runners 350 may bow outwardly by virtue of a cell 322 shortening, the same is not true of sub-annular runners 330. Thus, sub-annular runners 330 may be shape-set, such as by heat setting, so that in the absence of externally applied forces, runners 330 deflect or bow outwardly of the surface defined by struts 320e and 320f. When cuff 312 (FIG. 3A) is coupled to the abluminal surface of the inflow end 302 of stent 306, the cuff is substantially tubular when runners 330 are not bowed outwardly. When runners 330 bow outwardly on the expansion of heart valve 300, they form protuberances in cuff 312 to help anchor and seal heart valve 300 within the native valve annulus VA. In one example, runners 330 may extend between about 5 mm and about 10 mm radially outward from stent 302 in the absence of externally applied force. However, these dimensions are merely exemplary and other dimensions may be suitable depending on the exact location FIG. 3G illustrates prosthetic heart valve 300 disposed within a native valve annulus VA from which the native valve leaflets have been resected. When implanted within native valve annulus VA, runners 330 bow outwardly, for example as defined by their pre-set shape, and may be disposed below native valve annulus VA (i.e., in a sub-annular position). Runners 350 also bow outwardly and may be disposed, for example, above native valve annulus VA (i.e., in a supra-annular position). As shown in FIG. 3G, runners 330 are disposed such that they are in contact with the left ventricular outflow tract LVOT, while runners 350 are disposed between native valve annulus VA and coronary arteries CA. Similar to prosthetic valve 200, this positioning helps to provide a seal between prosthetic heart valve 300 and the native heart tissue, while also robustly anchoring prosthetic heart valve 300 above and below native valve annulus VA, preventing migration into left ventricle 124 or aorta 110. These anchoring features may be effective in a variety of patient populations, regardless of their native valve anatomy. For example, prosthetic heart valve 300 may provide anchoring in patients that have their native aortic valve leaflets partially or fully resected, as well as in patients with conditions such as aortic insufficiency in which the native aortic valve leaflets are not resected but provide suboptimal substrate quality for anchoring.

FIGS. 4A-D illustrate an exemplary sutureless method of replacing native aortic valve 132 with a prosthetic heart valve according to the present disclosure. Although the method illustrated and described is with reference to prosthetic heart valve 200, it should be understood that the method is equally applicable to the implantation of prosthetic heart valve 300, or other prosthetic heart valves having sub-annular and supra-annular features for anchoring the prosthetic heart valve and mitigating PV leak. In a first step, shown in FIG. 4A, prosthetic heart valve 200 is provided and is coupled to valve holder 400. Valve holder 400 may generally include a handle 410 for gripping by the surgeon, a base 420 for coupling to prosthetic heart valve 200, and a shaft 430 connecting the handle to the base. Base 420 may be coupled to outflow end 232 of stent 202 by sutures, for example. Valve holder 400 is merely one example of a valve holder, and other designs may be suitable for use with the prosthetic heart valves disclosed herein. For example, valve holder 400 may alternatively include a base that attaches to prosthetic heart valve 200 by means other than sutures, such as by corresponding releasable mating features on prosthetic heart valve 200 and base 420. Valve holder 400 may be provided with still other features, such as a base 420 that radially shrinks during delivery to provide the surgeon a better field of view of the implantation procedure.

Figure 4A:
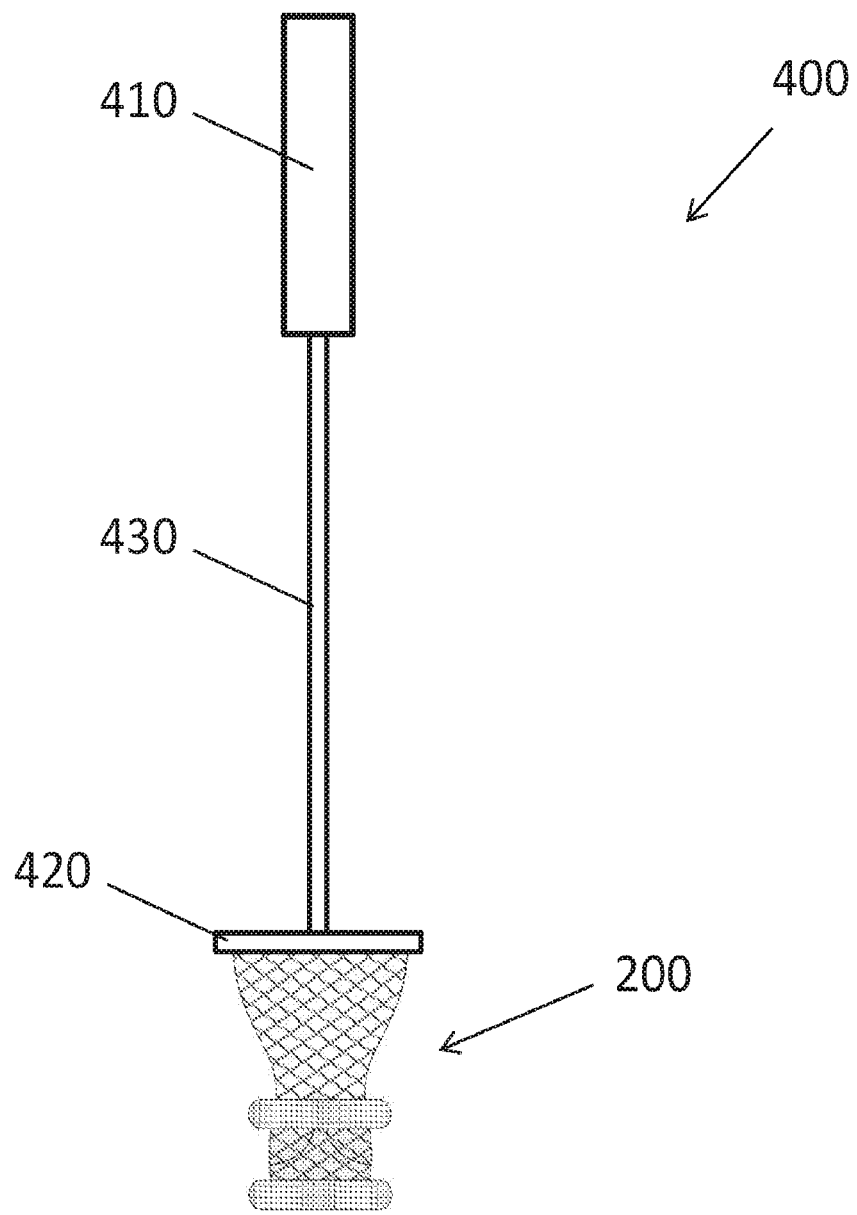
FIG. 4A is a highly schematic side view of a valve holder coupled to the prosthetic heart valve of FIG. 2A.
Figure 4B:
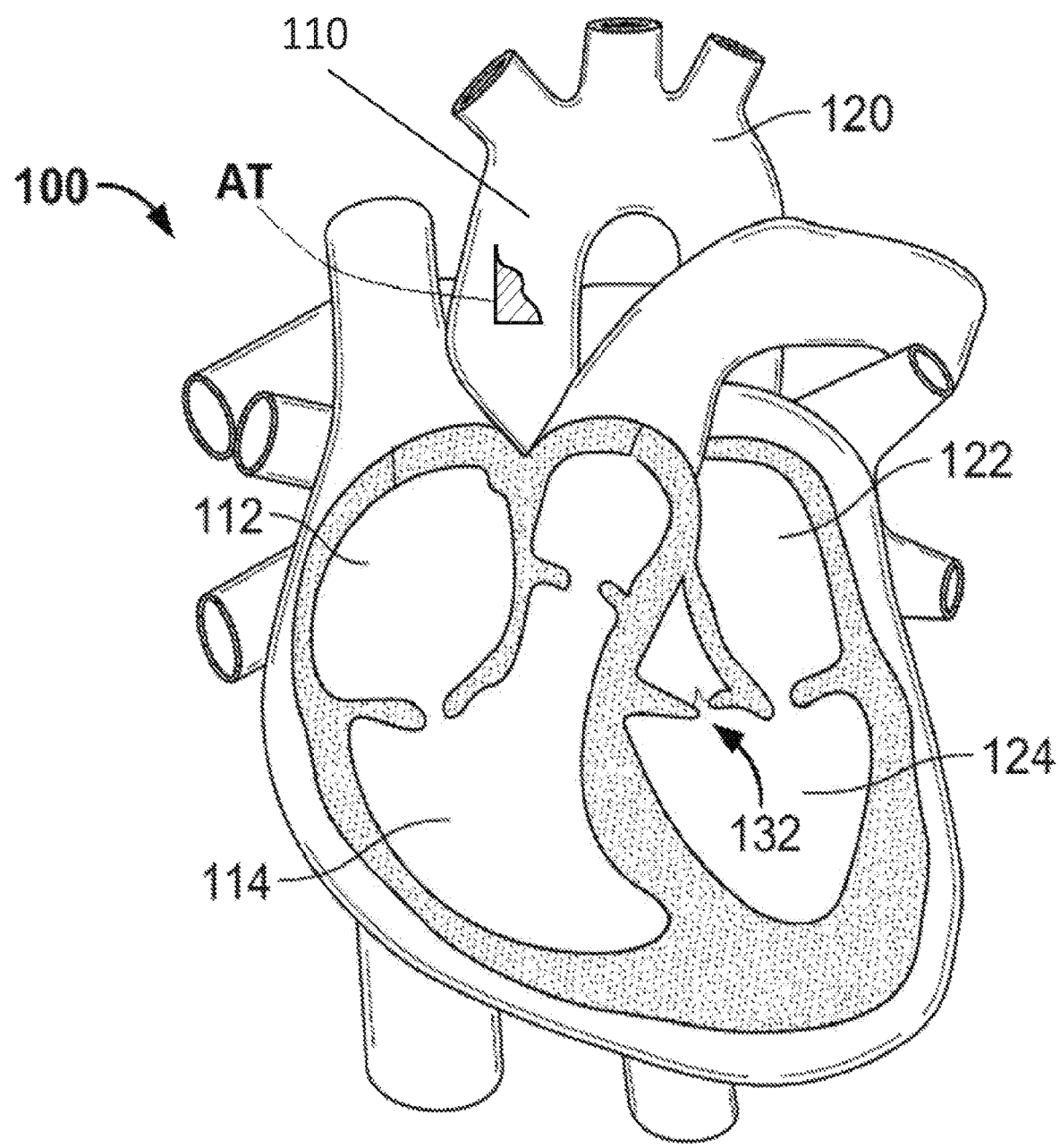
FIGS. 4B-D are highly schematic cutaway representations of a human heart showing a surgical method of delivering the prosthetic heart valve of FIG. 2A.

Before or after prosthetic heart valve 200 is coupled to valve holder 400, the patient may be put on cardiopulmonary bypass and the beating of heart 100 may be ceased. The time during which the patient remains on bypass is preferably minimized to the extent possible. As shown in FIG. 4B, once the patient is on bypass, an incision may be made in aorta 110 to provide direct access to aortic valve 132. For example, the surgeon may make an "L" shaped aortotomy AT in aorta 110. It should be understood that the heart 100 and location of the aortotomy AT in aorta 110 is not to scale. In fact, the incision in aorta 110 would preferably be closer to aortic valve 132 than shown to provide the least practical distance between the incision and the aortic valve. At this point, if desired, the surgeon may partially or fully resect the native leaflets of aortic valve 132, if the leaflets have not been resected in a prior procedure, such as a prior prosthetic valve implantation.

Figure 4C:
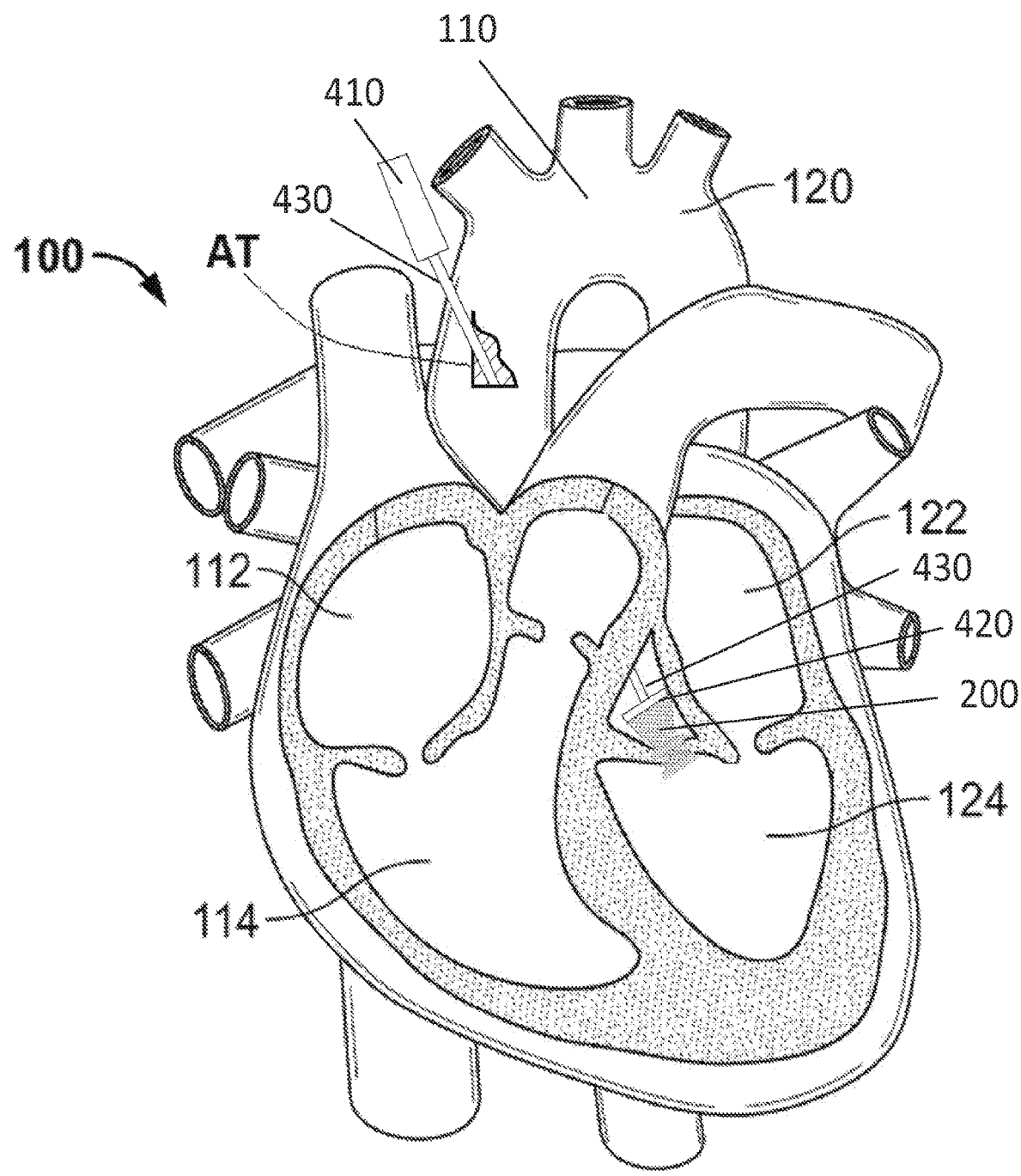
Figure 4D:
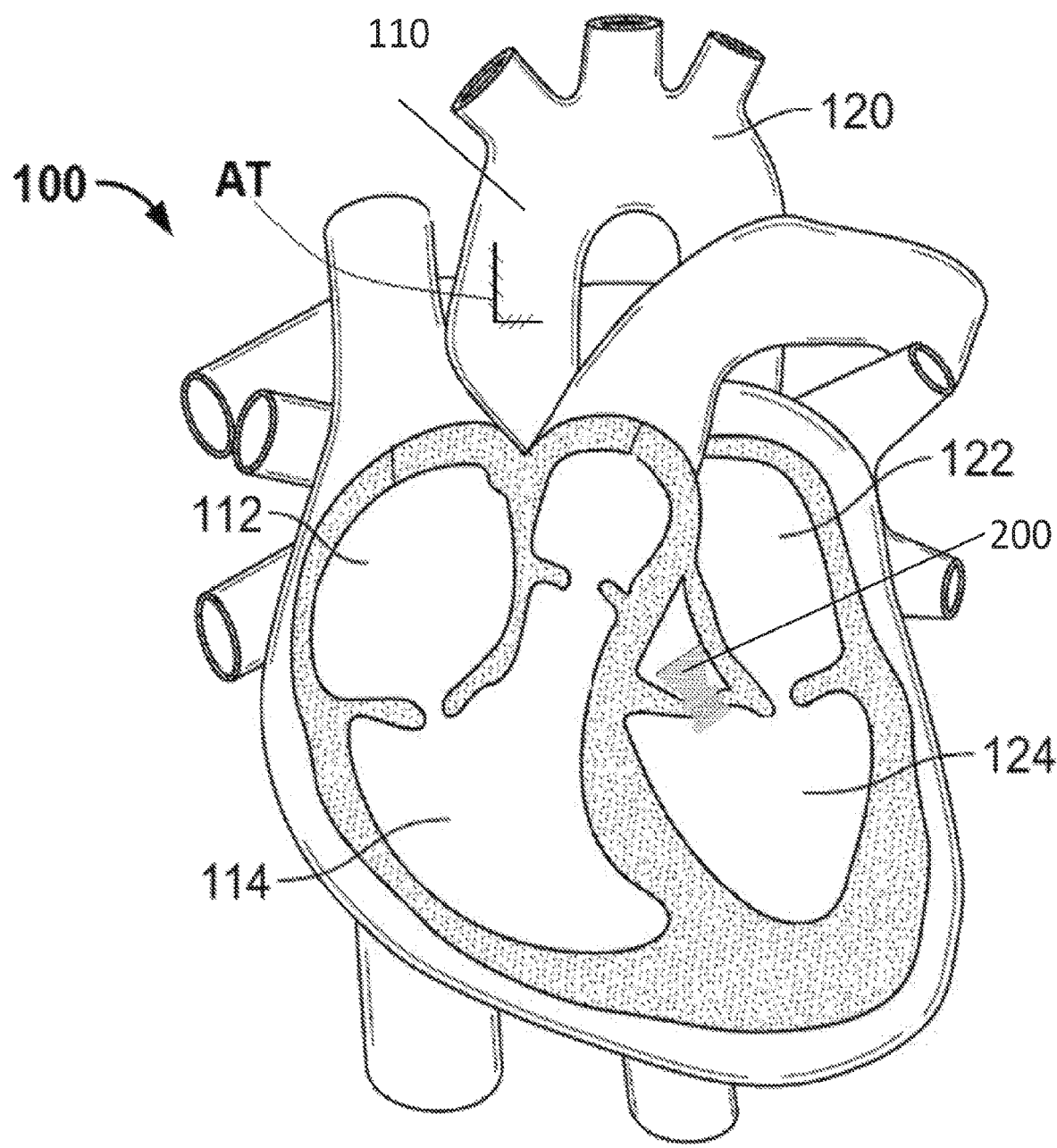

Once the incision has been made in aorta 110, and leaflets have been resected (if desired), the surgeon may grasp handle 410 of valve holder 400 and advance prosthetic heart valve 200 into aorta 110 and toward the annulus of aortic valve 132. The incision in aorta 110 may provide full or nearly full visualization of the procedure to the surgeon. With this full visualization, the surgeon may advance prosthetic heart valve 200 until native valve annulus VA is captured between sealing ring 250A and sealing ring 250B, as shown in FIG. 4C (also shown in FIG. 2C). Once properly positioned, the surgeon may disconnect prosthetic heart valve 200 from the base 420 of valve holder 400, for example by cutting one or more sutures connecting the prosthetic heart valve to the base. At this point, as shown in FIG. 4D, the surgeon may remove valve holder 400 from the patient's heart 100, suture aortotomy AT closed, take the patient off bypass, and restart the heart.

As should be clear from the description above, the implantation procedure, from the creation of aortotomy AT to the suturing of the aortotomy closed, is relatively simple and fast. This sutureless approach provides the surgeon full visualization of the procedure, and the surgeon is able to secure the prosthetic heart valve in native valve annulus VA without the need for suturing the prosthetic heart valve to the anatomy or any other additional procedures. In addition, the provision of sub-annular sealing ring 250A and supra-annular sealing ring 250B in prosthetic heart valve 200 helps ensure that there is no paravalvular leakage once the heart starts beating again, and that the prosthetic heart valve 200 remains robustly anchored in native valve annulus VA, even if the native valve leaflets have been resected or if the patient has native valve leaflets that do not provide a suitable substrate for anchoring. The identical or nearly identical procedure would be used for prosthetic heart valve 300, with the exception that sub-annular runners 330 and supra-annular runners 350 would provide the anchoring and sealing between native valve annulus VA and prosthetic heart valve 300.

Figure 5:
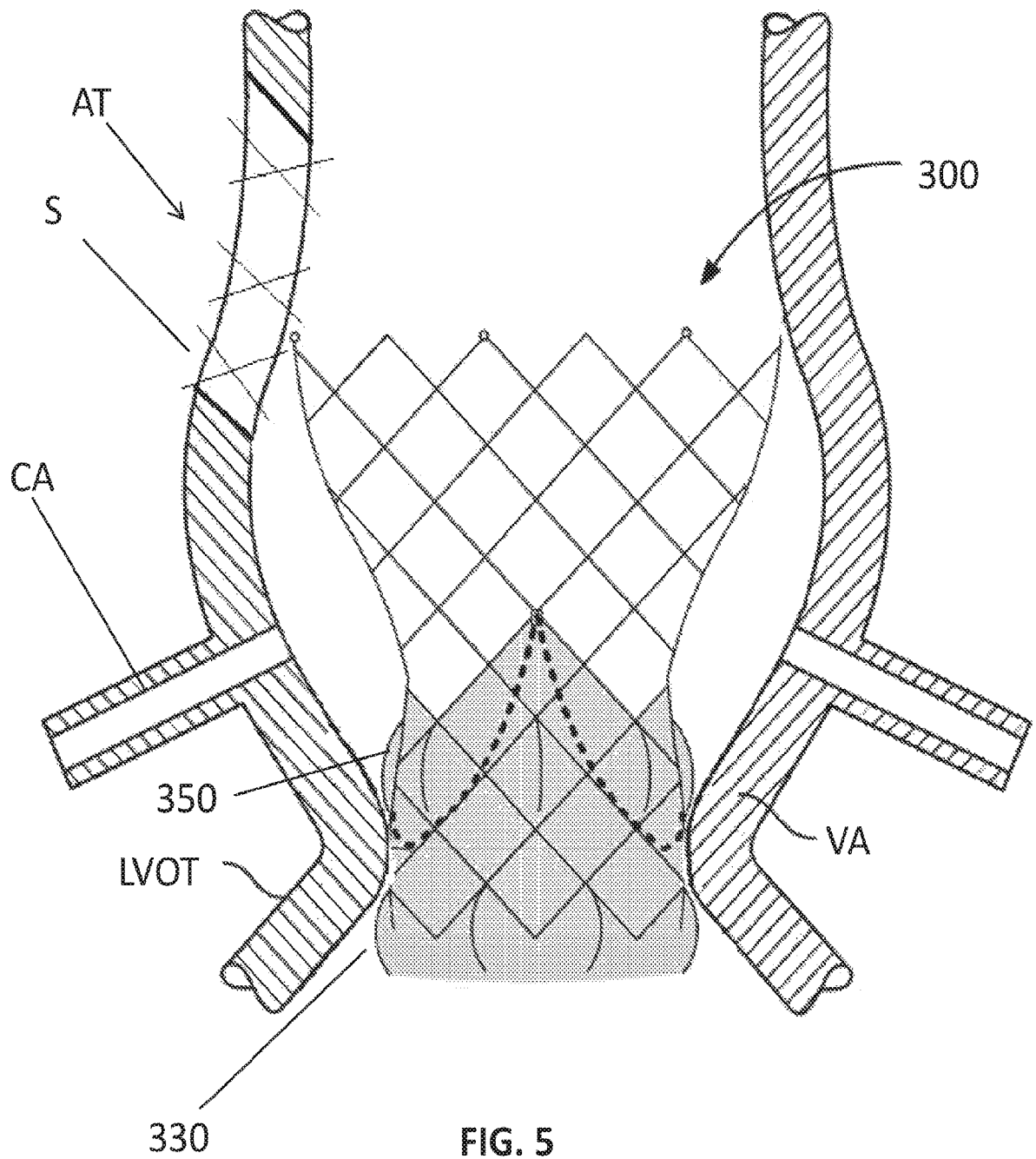
FIG. 5 is a highly schematic side view of the heart valve of FIG. 3A implanted into a native valve annulus with resected native valve leaflets after completion of the implantation procedure.

Although the implantation of prosthetic heart valves 200 and 300 has been described with reference to the sutureless approach, it should be understood that because prosthetic heart valves 200 and 300 are collapsible and expandable, a transcatheter delivery approach may also be employed. A transcatheter approach may provide, for example, a less invasive procedure and eliminate the need for a patient to be put on bypass. However, a transcatheter approach requires imaging technology to determine where the prosthetic heart valve is in relation to the patient's anatomy. On the other hand, and as noted above, the sutureless approach may provide for full visualization to the surgeon through the incision. It will also be appreciated that prosthetic heart valves 200 and 300 may be implanted using a full surgical approach in which the prosthetic heart valve is sutured in place in the native valve annulus. As noted previously, such procedure is much more time-consuming and creates a greater risk of infection As noted above, the location of aortotomy AT shown in FIGS. 4B-D is for purposes of illustration, and the incision preferably would be made closer to aortic valve 132. FIG. 5 shows prosthetic heart valve 300 positioned in native valve annulus VA of a patient, after aortotomy AT has been closed with one or more sutures S. FIG. 5 better illustrates the relative positioning between the incision made in aorta 110 and the implanted prosthetic heart valve 300. Depending on the exact location of aortotomy AT, it is possible that, after implantation, a portion of prosthetic heart valve 300, such as aortic section 342 and portions of transition section 341, may abut or otherwise contact the closed aortotomy AT. This position may be undesirable because contact between prosthetic heart valve 300 and closed aortotomy AT may prevent healing of the incision site, or may cause injury such as interfering with sutures S or reopening of the incision.

Figure 6A:
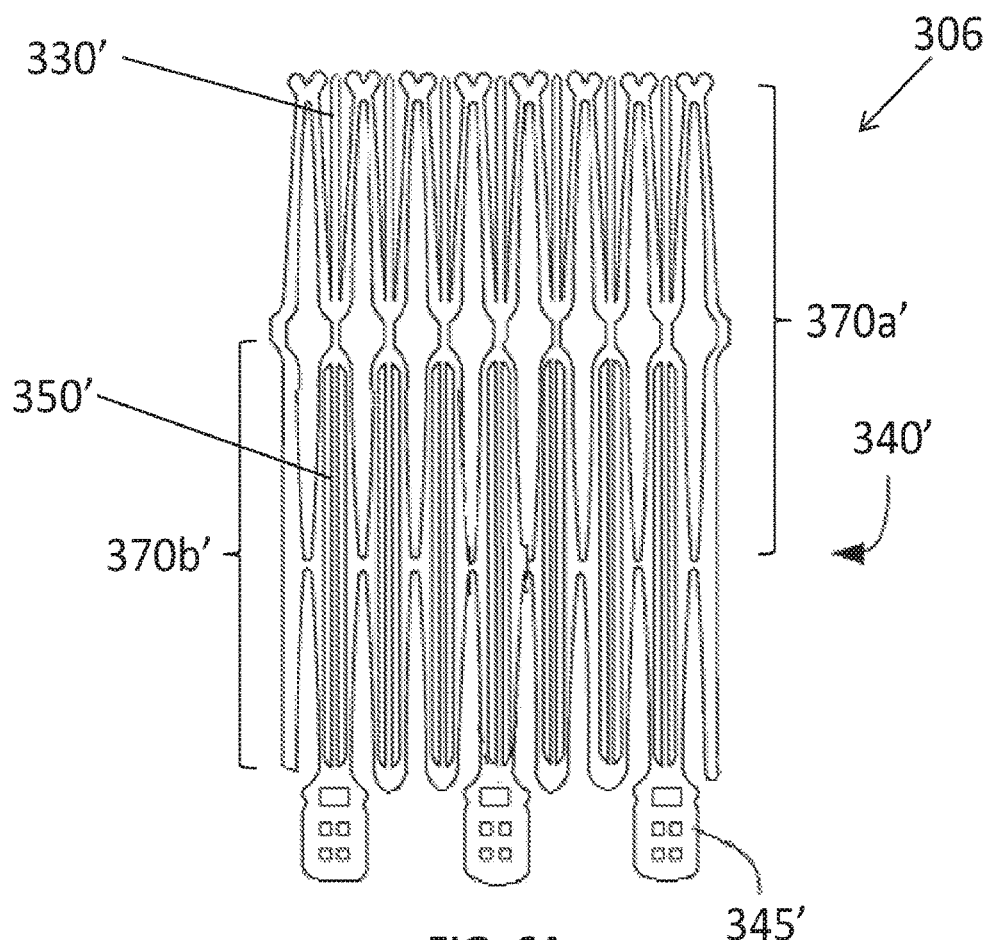
FIG. 6A is a developed view of a stent of another embodiment of a heart valve in the collapsed configuration.

To minimize the likelihood of irritation of the closed aortotomy AT after implantation, stent 306 may be formed without aortic section 342 and some or all of transition section 341. For example, FIG. 6A illustrates stent 306' for use with a prosthetic heart valve 300' according to another embodiment, the stent being in a collapsed and flattened configuration. It should be understood that prosthetic heart valves 300 and 300' may be identical in all respects, with the exception that stent 306' has a shorter length than stent 306. As shown in FIG. 6A, stent 306' includes first and second rows of cells 370a-b. Similar to prosthetic heart valve 300, prosthetic heart valve 300' may include a valve assembly 308' identical to valve assembly 308 and coupled to commissure attachment features 345'. Prosthetic heart valve 300' may also include a cuff 312' identical to cuff 312 of prosthetic heart valve 300. Stent 306' is configured so that it has an annulus section 340', but no aortic section (flared or otherwise). In addition, stent 306' includes sub-annular runners 330' and supra-annular runners 350' that are similar or identical to sub-annular runners 330 and supra-annular runners 350 of stent 306.

Figure 6B:
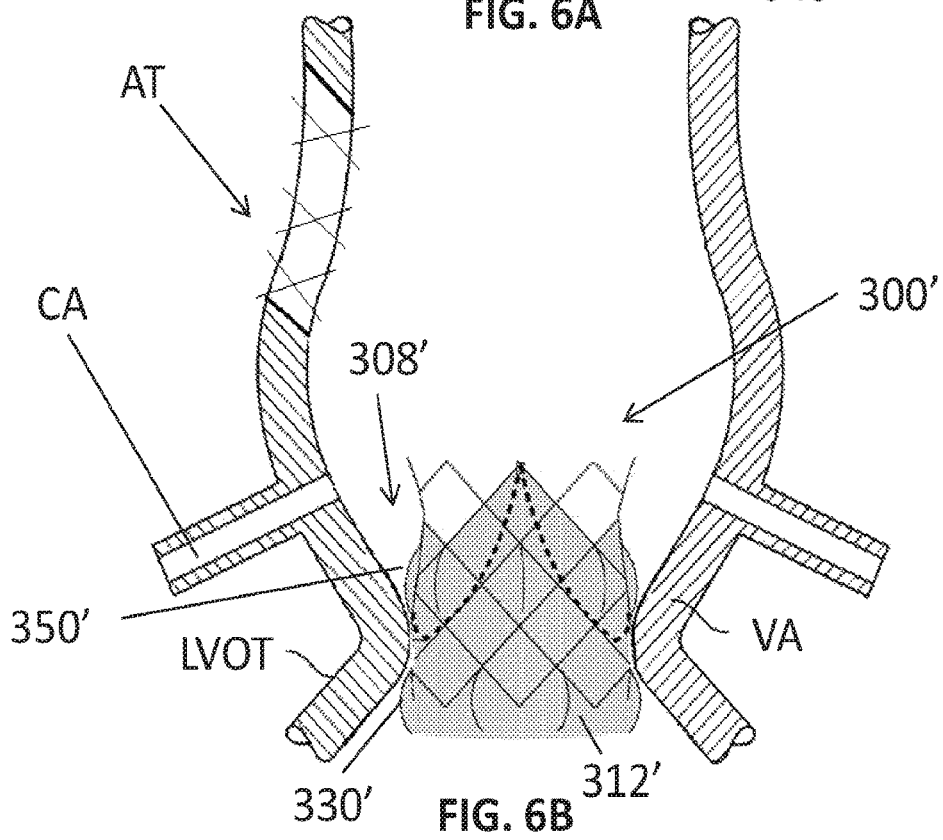
FIG. 6B is a highly schematic side view of a heart valve incorporating the stent of FIG. 6A implanted into a native valve annulus with resected native valve leaflets after completion of the implantation procedure.

FIG. 6B illustrates prosthetic heart valve 300' implanted in native valve annulus VA, with runners 330' and runners 350' anchoring the prosthetic heart valve on each side of the native valve annulus. With the configuration of stent 306' described above, the axial length of stent 306' is shorter than that of stent 306, and may reduce or eliminate the likelihood that any part of prosthetic heart valve 300' rubs, contacts, or otherwise interferes with closed aortotomy AT after implantation. In general, a flared aortic section, such as aortic section 342 of stent 306, may provide some amount of anchoring and resistance to migration of the stent into left ventricle 124, and may further facilitate the axial centering of the stent with respect to the axial center of native valve annulus VA. However, the robust anchoring provided by runners 330' and 350' about native valve annulus VA may make it unnecessary to have a flared aortic section. Prosthetic heart valve 300' may be delivered and implanted in the same manner as described above with respect to prosthetic heart valve 200.

Figure 7:
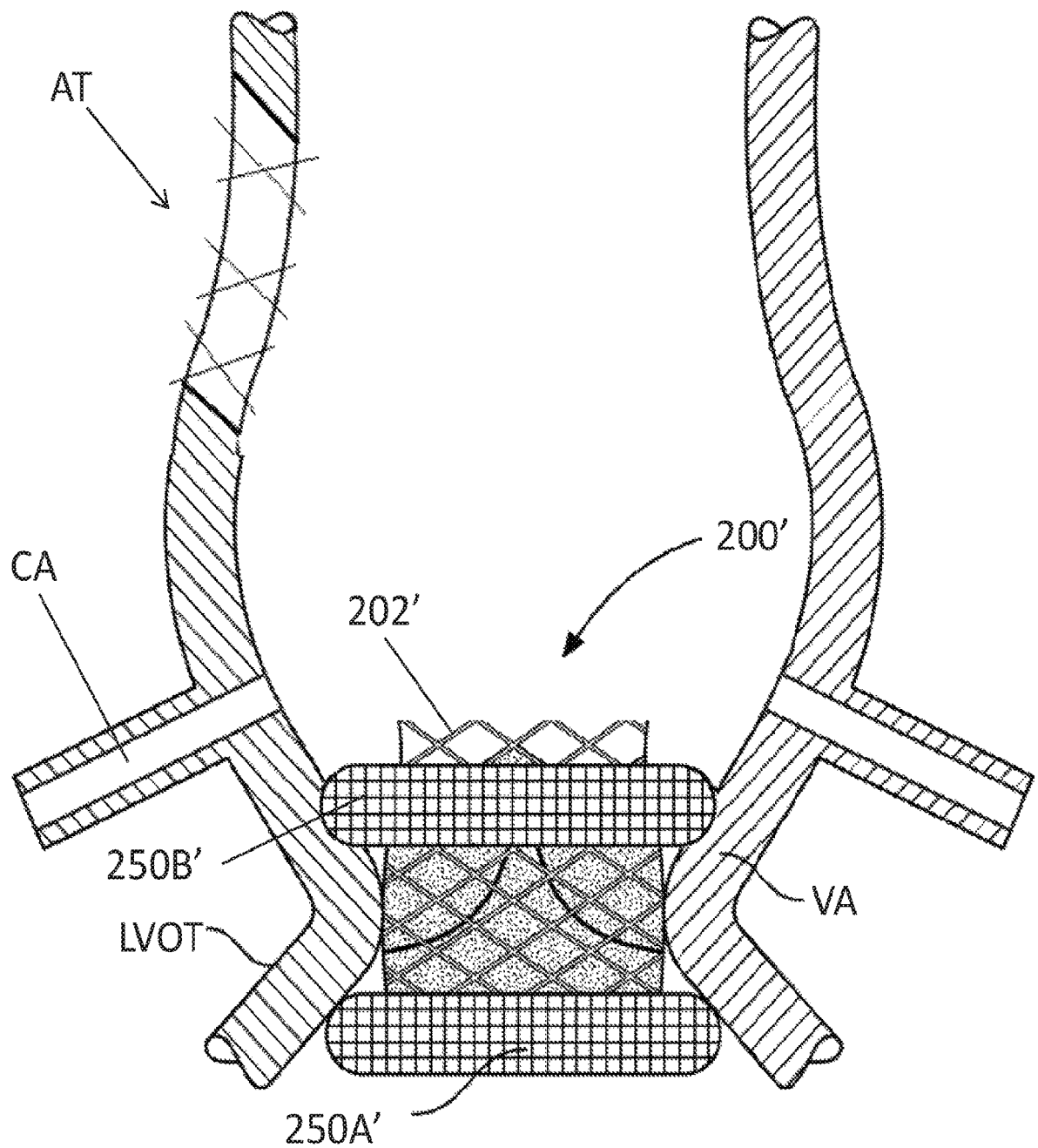
FIG. 7 is a highly schematic side view of a heart valve according to another embodiment implanted into a native valve annulus with resected native valve leaflets after completion of the implantation procedure.

Modifications that are the same as or similar to those made to prosthetic heart valve 300 to form prosthetic heart valve 300' may be made to prosthetic heart valve 200. For example, FIG. 7 shows prosthetic heart valve 200' implanted in native valve annulus VA, with sub-annular sealing ring 250A' and supra-annular sealing ring 250B' capturing and anchoring the prosthetic heart valve to the native valve annulus. Prosthetic heart valve 200' may be identical to prosthetic heart valve 200 in all respects, with the exception that stent 202' includes only an annulus section so that it is shorter than stent 202, reducing the likelihood of prosthetic heart valve 200' irritating or interfering with closed aortotomy AT. Prosthetic heart valve 200' may be delivered and implanted in the same manner as described above with respect to prosthetic heart valve 200.

It should be understood that features of one embodiment may be combined or replaced with features of other embodiments described herein. For example, a prosthetic heart valve may include either the long stent of prosthetic heart valves 200 and 300, or the short stent of prosthetic heart valves 200' and 300'. Regardless of the type of stent employed, the prosthetic heart valve may have a supra-annular sealing and anchoring feature in the form of either the sealing ring 250B of prosthetic heart valve 200, or the runner 350 of prosthetic heart valve 300. Similarly, the prosthetic heart valve may also include a sub-annular sealing and anchoring feature in the form of either the sealing ring 250A of prosthetic heart valve 200, or the runner 330 of prosthetic heart valve 300. Thus, a prosthetic heart valve may include a combination of a sealing ring 250A and runners 350 or a combination of a sealing ring 250B and runners 330, and these combinations may be present on either a long stent or a short stent as described herein.

According to one embodiment of the disclosure, a prosthetic heart valve for replacing a native valve includes a stent extending between an inflow end and an outflow end, the stent including an annulus section adjacent the inflow end, a plurality of first struts connected to the stent and configured to extend radially outwardly from the stent when in a relaxed condition, and a plurality of second struts connected to the stent and configured to extend radially outwardly from the stent when in the relaxed condition, the plurality of first struts being spaced from the plurality of second struts in a longitudinal direction of the stent; and a valve assembly disposed within the stent; and/or the valve assembly may include a cuff disposed around an exterior of the annulus section and covering the plurality of first struts and the plurality of second struts; and/or the prosthetic heart valve may include a plurality of third struts forming cells, each of the first struts being nested within one of the cells when the stent is in a collapsed condition; and/or the prosthetic heart valve may include a plurality of third struts forming cells, each of the second struts having a first end connected to at least one of the third struts; and/or each of the second struts may have a free end; and/or the stent may be collapsible and expandable; and/or the plurality of first struts may be positioned closer to the outflow end of the stent than the plurality of second struts.

According to another embodiment of the disclosure, a prosthetic heart valve includes a stent extending from an inflow end to an outflow end; a first sealing ring coupled to the stent adjacent the inflow end of the stent, the first sealing ring comprising a first tube extending circumferentially around the stent; a second sealing ring coupled the stent, the second sealing ring comprising a second tube extending circumferentially around the stent, the second sealing ring being spaced from the first sealing ring in a longitudinal direction of the stent; and a valve assembly disposed within the stent; and/or the first tube may include a first wire coiled into a first repeating shape and the second tube may include a second wire coiled into a second repeating shape; and/or the first and second repeating shapes may be selected from the group consisting of a rectangular shape and a diamond shape; and/or the first wire may have a first thickness and the second wire may have a second thickness less than the first thickness; and/or one of the first and second tubes may be formed of a braided mesh; and/or the stent may be collapsible and expandable.

A further embodiment of the disclosure provides a method of implanting a prosthetic heart valve in a patient, the prosthetic heart valve including a first valve anchoring feature spaced apart from a second valve anchoring feature. The method includes inserting the prosthetic heart valve into the patient's cardiovascular system while coupled to a valve holder; advancing the prosthetic heart valve to a position adjacent a native valve annulus in the patient so that the first valve anchoring feature is disposed on a first side of the native valve annulus and the second valve anchoring feature is disposed on a second side of the native valve annulus opposite the first side; releasing the prosthetic heart valve from the valve holder; and removing the valve holder from the patient; and/or the method may further include making an incision in the aorta of the patient prior to inserting the prosthetic heart valve into the patient's cardiovascular system; and closing the incision after removing the valve holder from the patient, wherein, after the closing step, the prosthetic heart valve does not contact the closed incision; and/or the prosthetic heart valve may have an expanded condition and a collapsed condition, and the inserting step may include inserting the prosthetic heart valve into the patient's cardiovascular system in the expanded condition; and/or the first valve anchoring feature may be selected from the group consisting of a sealing ring attached to a stent of the prosthetic heart valve and configured to extend radially outward from the stent and a strut attached to the stent and configured to extend radially outward from the stent; and/or the second valve anchoring feature may be selected from the group consisting of a sealing ring attached to the stent and configured to extend radially outward from the stent and a strut attached to the stent and configured to extend radially outward from the stent.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of implanting a prosthetic heart valve in a patient, the prosthetic heart valve including a first valve anchoring feature spaced apart from a second valve anchoring feature, and having an expanded condition and a collapsed condition, the method comprising:

making an incision in an aorta of the patient;

inserting the prosthetic heart valve into the patient's cardiovascular system through the incision in the aorta while the prosthetic heart valve is coupled to a valve holder and while the prosthetic heart valve is in the expanded condition;

advancing the prosthetic heart valve to a position adjacent a native valve annulus in the patient so that the first valve anchoring feature is disposed on a first side of the native valve annulus and the second valve anchoring feature is disposed on a second side of the native valve annulus opposite the first side;

releasing the prosthetic heart valve from the valve holder;

removing the valve holder from the patient; and closing the incision after removing the valve holder from the patient, wherein, after the incision is closed, the prosthetic heart valve does not contact the closed incision.

2. The method of claim 1, wherein the first valve anchoring feature is selected from the group consisting of a sealing ring attached to a stent of the prosthetic heart valve and configured to extend radially outward from the stent and a strut attached to the stent and configured to extend radially outward from the stent.

3. The method of claim 2, wherein the second valve anchoring feature is selected from the group consisting of a sealing ring attached to the stent and configured to extend radially outward from the stent and a strut attached to the stent and configured to extend radially outward from the stent.

4. The method of claim 1, wherein the prosthetic heart valve includes a collapsible and expandable stent and a valve assembly positioned within the stent.

5. The method of claim 4, wherein the stent is self-expanding.

6. The method of claim 1, wherein the prosthetic heart valve is coupled to the valve holder with sutures.

7. The method of claim 1, wherein an outflow end of the prosthetic heart valve is coupled to a distal end of a base of the valve holder, the base of the valve holder being adapted to radially shrink.

8. The method of claim 1, wherein the incision in the aorta is an "L"-shaped aortotomy.

9. The method of claim 1, wherein, after the incision is closed, the prosthetic heart valve is held in place without assistance from sutures coupling the prosthetic heart valve to the native valve annulus.

* * * * *